United States Patent
Ito et al.

(10) Patent No.: US 10,575,505 B2
(45) Date of Patent: Mar. 3, 2020

(54) HUMAN IL-15-SECRETING IMMUNODEFICIENT MOUSE

(71) Applicant: Central Institute for Experimental Animals, Kanagawa (JP)

(72) Inventors: Mamoru Ito, Kanagawa (JP); Ikumi Katano, Kanagawa (JP)

(73) Assignee: Central Institute for Experimental Animals, Kanagawa (JP)

( * ) Notice: Subject to any disclaimer, the term of this patent is extended or adjusted under 35 U.S.C. 154(b) by 0 days.

(21) Appl. No.: 15/575,988

(22) PCT Filed: Apr. 20, 2016

(86) PCT No.: PCT/JP2016/002112
§ 371 (c)(1),
(2) Date: Apr. 18, 2018

(87) PCT Pub. No.: WO2016/189799
PCT Pub. Date: Dec. 1, 2016

(65) Prior Publication Data
US 2018/0213755 A1    Aug. 2, 2018

(30) Foreign Application Priority Data

May 27, 2015 (JP) ................................ 2015-107932

(51) Int. Cl.
*A01K 67/027* (2006.01)
*C07K 14/54* (2006.01)
*C12N 15/85* (2006.01)

(52) U.S. Cl.
CPC ...... *A01K 67/0278* (2013.01); *C07K 14/5443* (2013.01); *C12N 15/8509* (2013.01); *A01K 2207/12* (2013.01); *A01K 2207/15* (2013.01); *A01K 2217/052* (2013.01); *A01K 2227/105* (2013.01); *A01K 2267/01* (2013.01); *A01K 2267/03* (2013.01); *C12N 2015/8518* (2013.01)

(58) Field of Classification Search
USPC .......................................................... 800/18
See application file for complete search history.

(56) References Cited

U.S. PATENT DOCUMENTS 7,145,055 B2   12/2006   Ito et al.
2017/0088597 A1 *  3/2017   Wong ..................... A61K 35/17

FOREIGN PATENT DOCUMENTS

WO    2011/002727    1/2011

OTHER PUBLICATIONS

Sato, "Development of an IL-15-Autocrine CD8 T-cell Leukemia in IL-15 Transgenic mice." Blood 2011, p. 4032.*
Seiji (J. Clin. Immunol., 2011, vol. 31, No. 6, p. 1038-1044).*
Bosma et al., "A Severe Combined Immunodeficiency Mutation in the Mouse." Nature, Feb. 10, 1983, 301 (5900); pp. 527-430, Abstract Only, 1 page.
Ito et al., "NOD/SCID/$\gamma_c^{null}$ Mouse: An Excellent Recipient Mouse Model for Engraftment of Human Cells." Hematopoiesis, Blood, Nov. 1, 2002, vol. 100, No. 9, pp. 3175-3182.
Katano et al., "Predominant Development of Mature and Functional Human NK Cells in a Novel Human IL-2-Producing Transgenic NOG Mouse." *The Journal of Immunology*, 2015, downloaded from http://www.jimmunol.org on Nov. 21, 2017, pp. 3513-3525.
Katano et al., "Long-term Maintenance of Human Mature NK Cells in human Interleukin-15 Transgenic NOG Mice." Japanese Association for Laboratory Science, Apr. 30, 2015, vol. 62, p. 204, Partial Translation, 4 pages.
Makino et al., "Breeding of a Non-obese, Diabetic Strain of Mice." Jikken Dobutsu, PubMed-NCBI, Jan. 1980, 29(1) pp. 1-13, Abstract Only, 1 page.
Notification of Transmittal of Translation of the International Preliminary Report on Patentability and the English Translation of the International Preliminary Report on Patentability issued by the International Bureau of WIPO for International Application No. PCT/JP2016/002112 dated Dec. 7, 2017, 8 pages.
Ogasawara, Kouetsu, "Biology of NK Cells." Tohoku University Dental Journal, 29, 2010, pp. 1-12, 13 pages, Partial Translation.

* cited by examiner

*Primary Examiner* — Michael C Wilson
(74) *Attorney, Agent, or Firm* — Occhiuti & Rohlicek LLP

(57) ABSTRACT

An object of the present invention is to provide a mouse that enables the functions of human NK cell to be studied. A DNA consisting of a nucleotide sequence represented by SEQ ID NO: 1, which is a gene region comprising a DNA in which a cDNA sequence encoding interleukin 15 (IL-15) is operably ligated to a cDNA sequence encoding the signal peptide of human interleukin (IL-2), is inserted to immunodeficient mouse cDNA. In NOD-scid, IL-2r$\gamma^{null}$-hIL-15 Tg mice thus generated, hCD56$^+$ cell having a concentration sufficient for conducting in vivo study on human mature NK cell are detected for at least 6 months after transplantation.

6 Claims, 11 Drawing Sheets
Specification includes a Sequence Listing.

[Figure 1]
(a)
GenBank Accession #: U02451
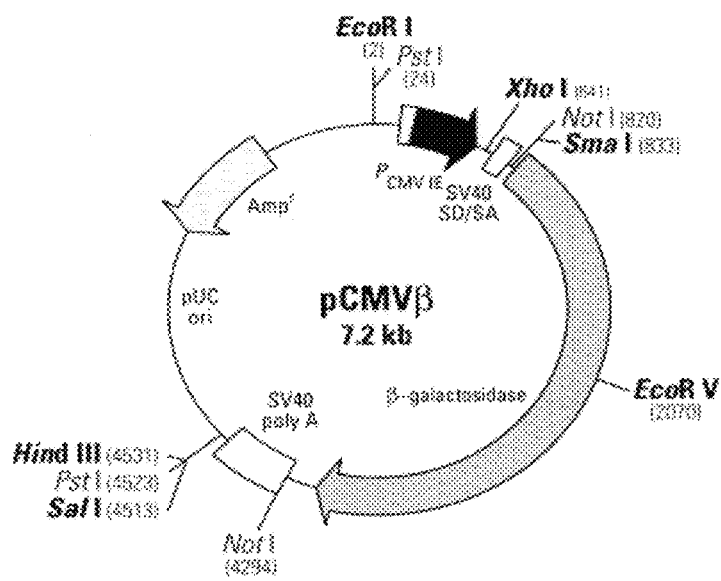
(b)
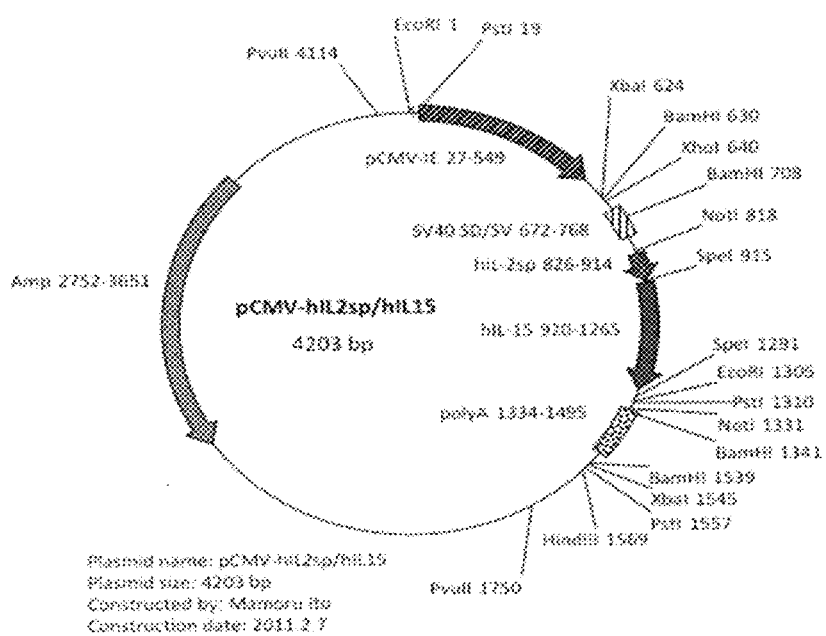

[Figure 2]
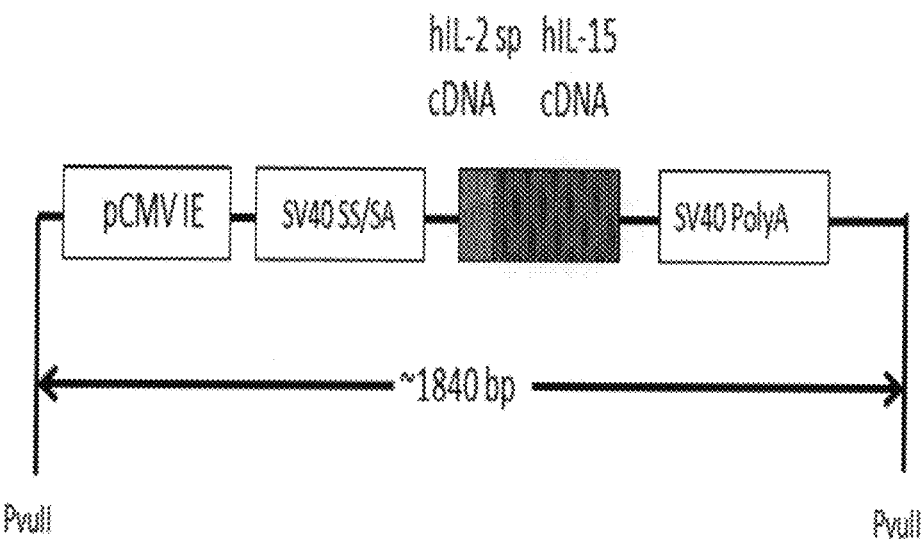
[Figure 3]
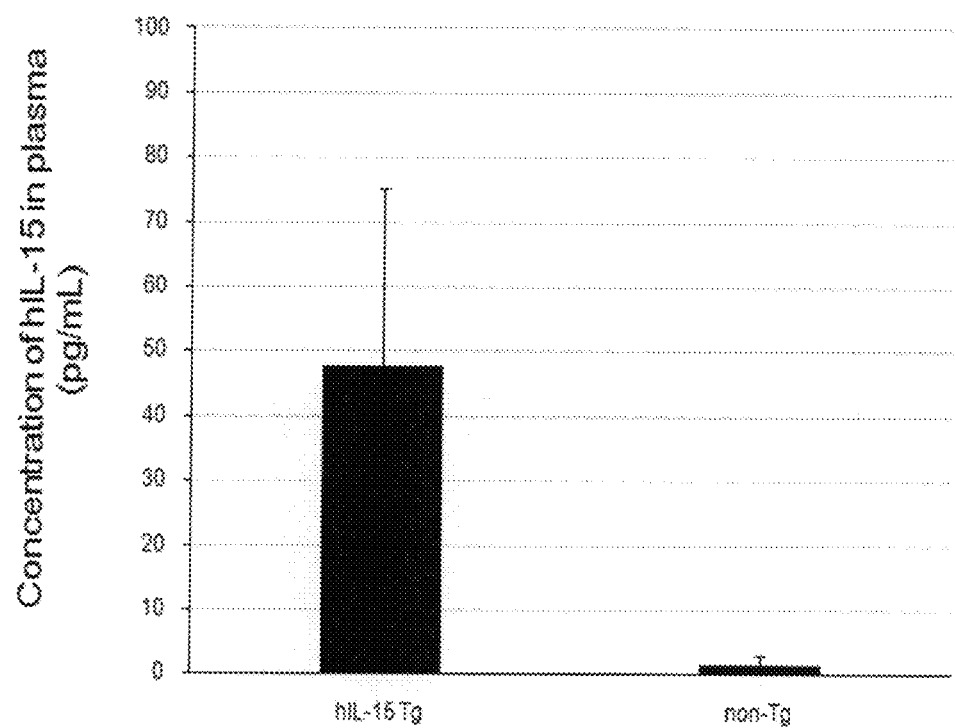

[Figure 4]
(a)
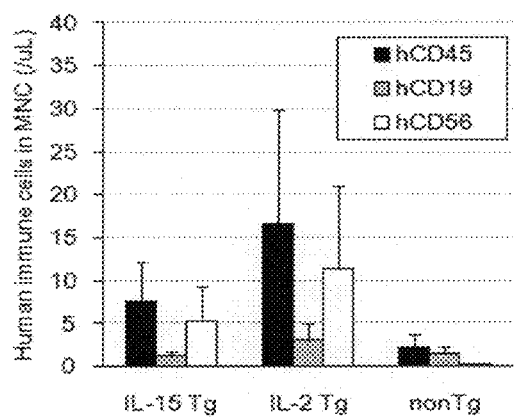
(b)
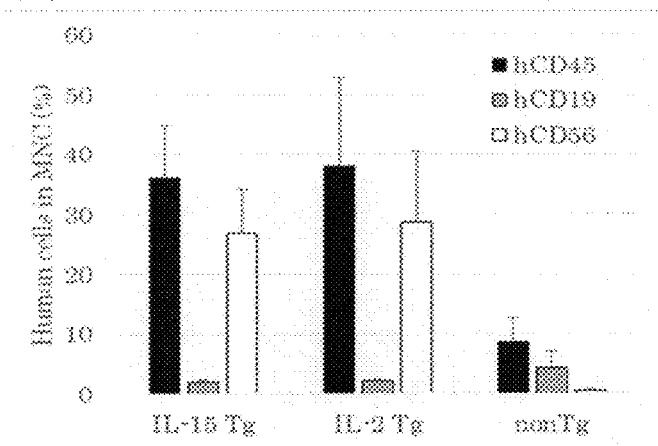
[Figure 5]
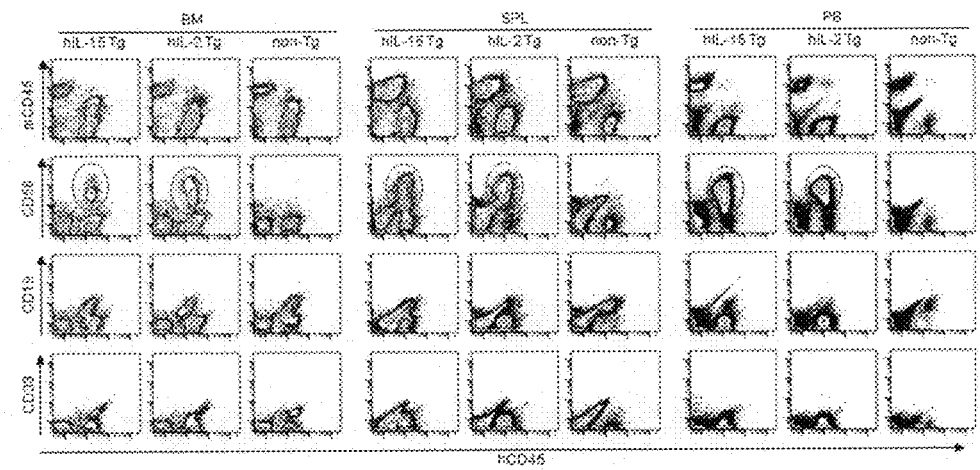

[Figure 6]
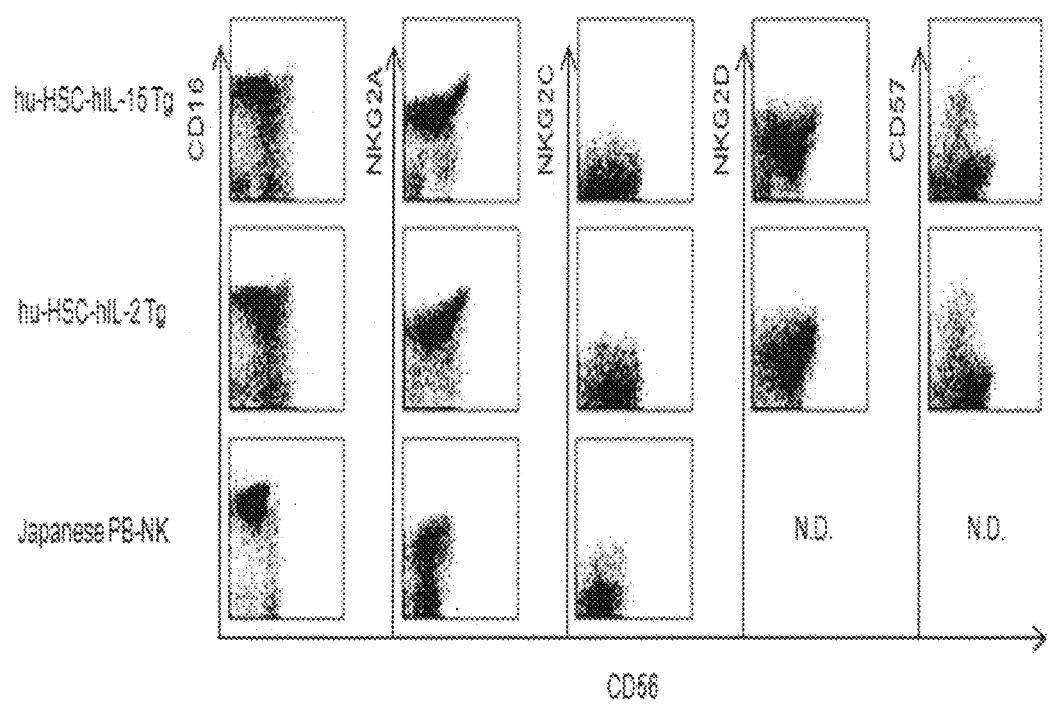
[Figure 7]
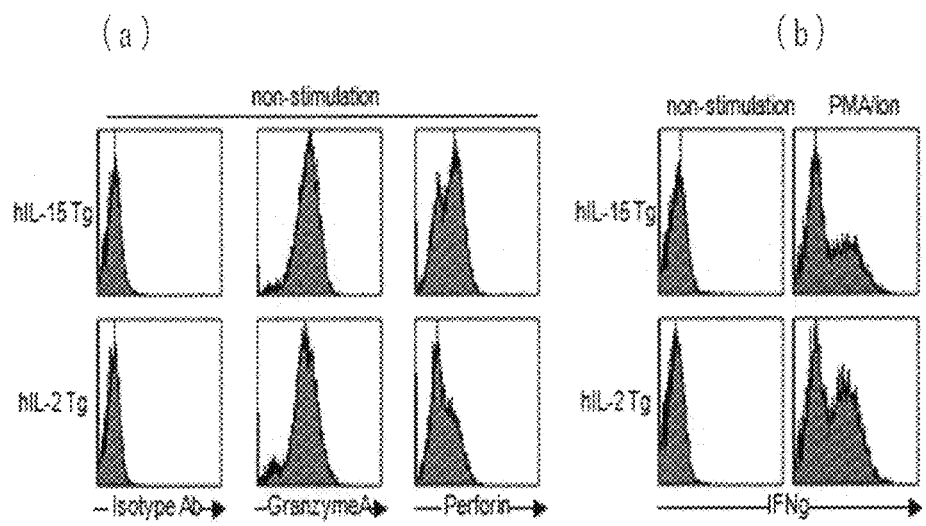

[Figure 8]
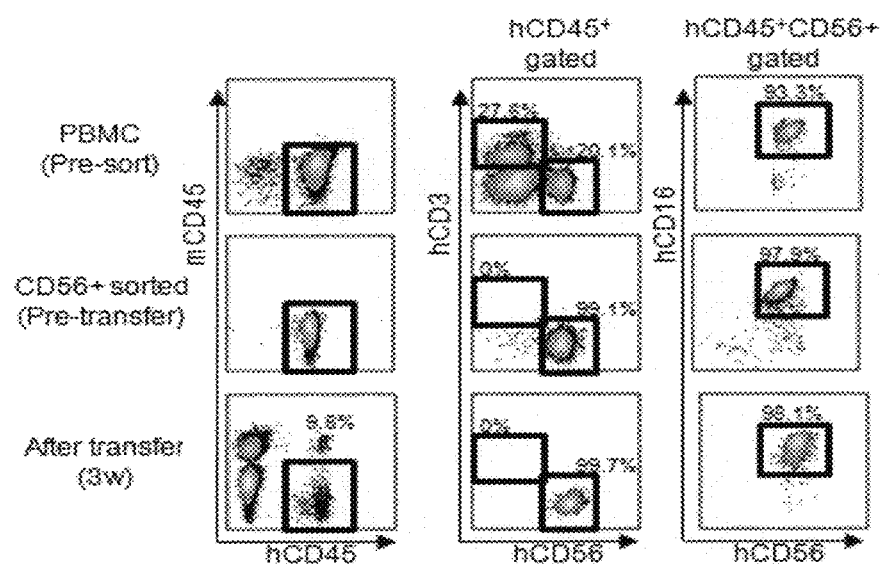

[Figure 9]
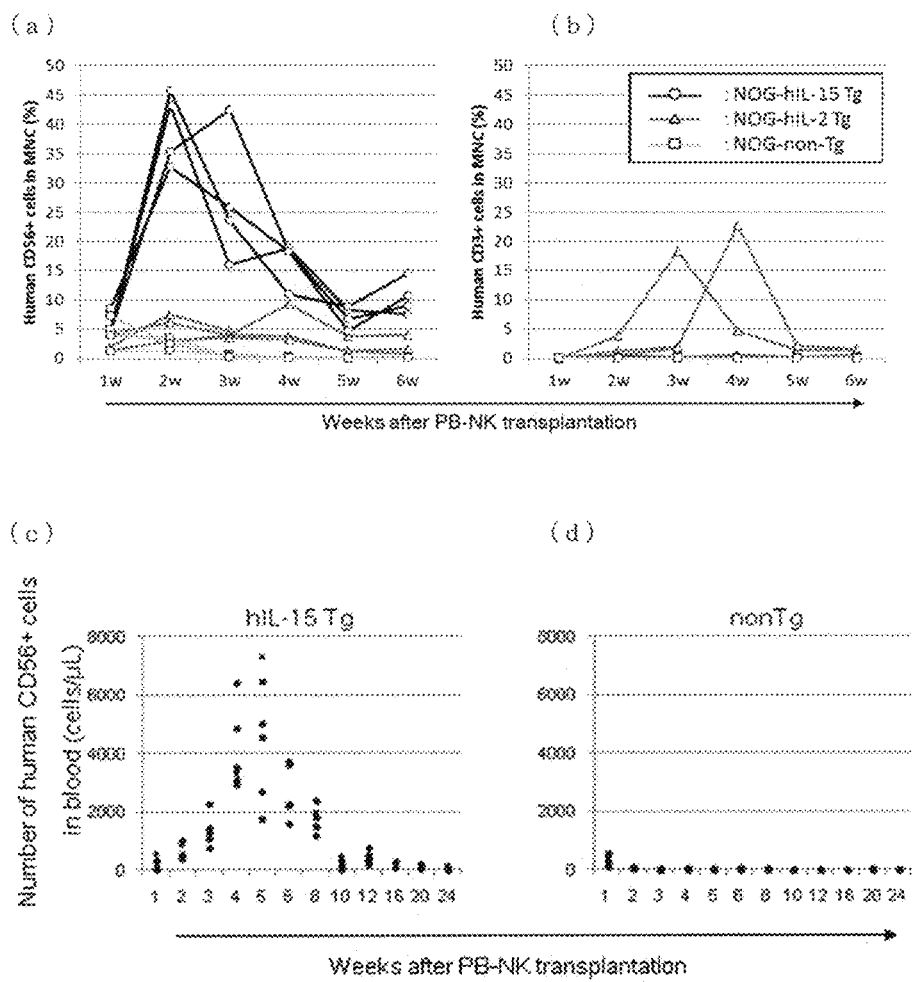

[Figure 10]
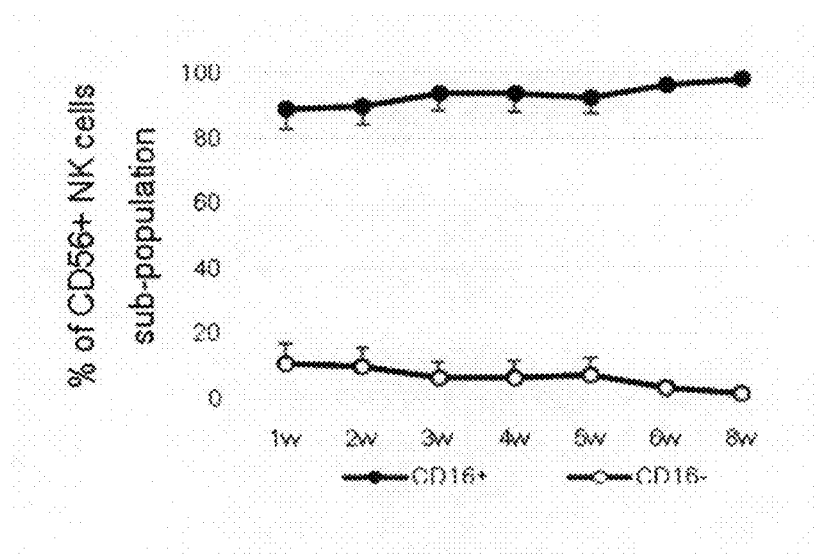
[Figure 11]
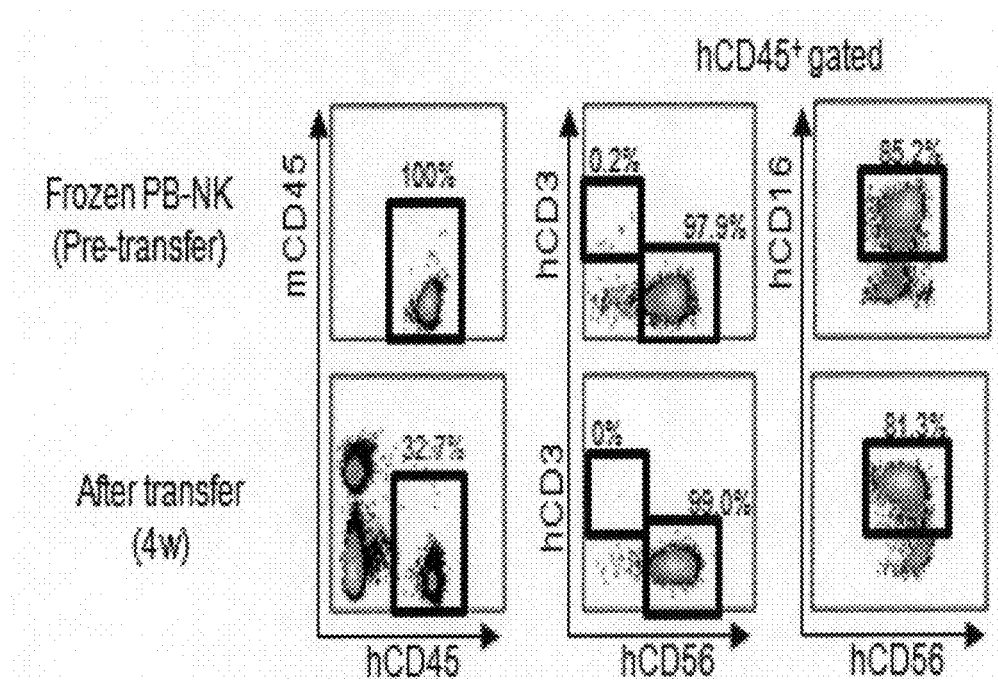

[Figure 12]
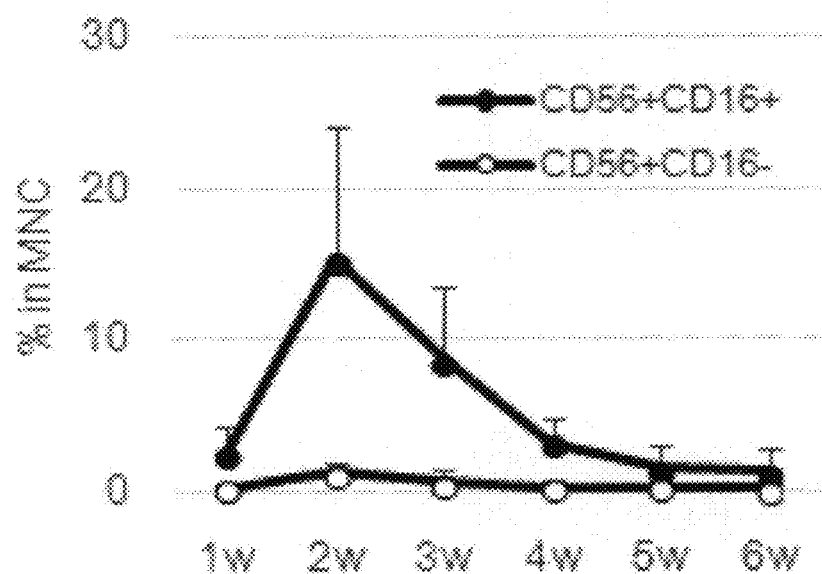
[Figure 13]
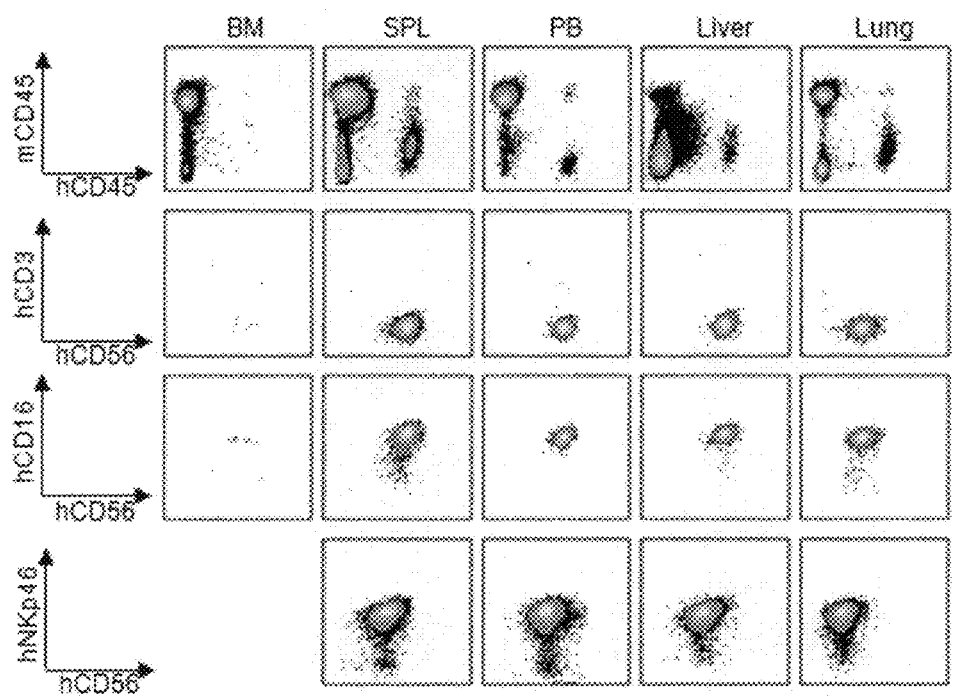

[Figure 14]
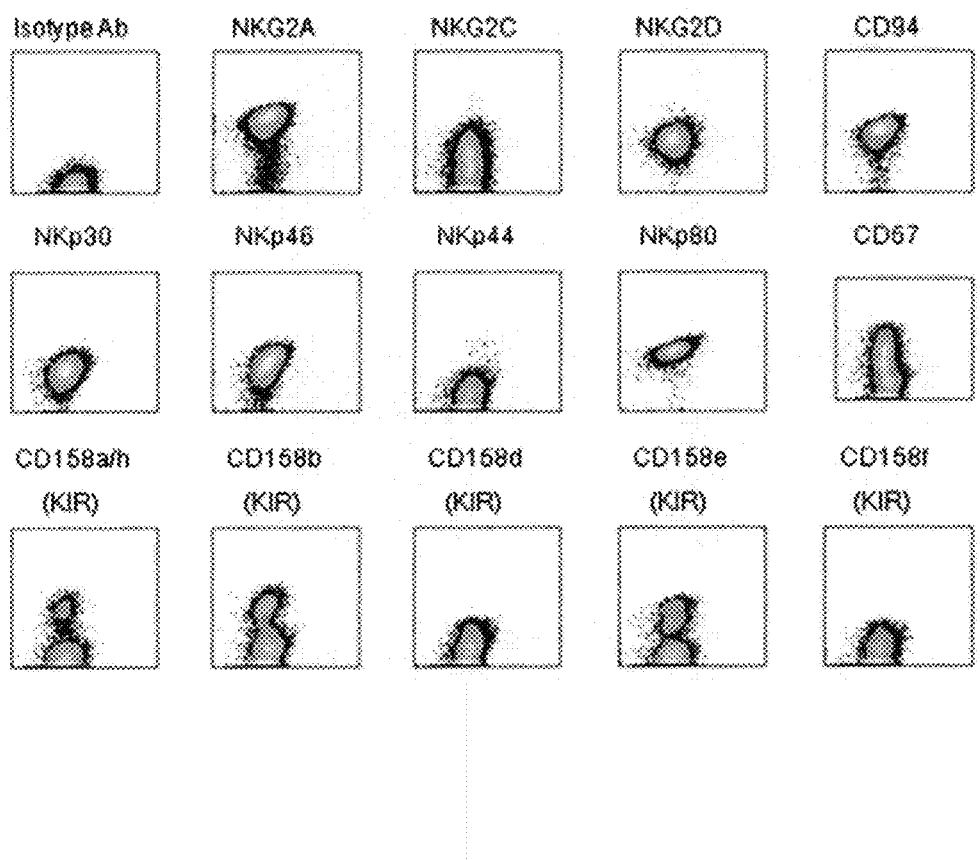

[Figure 15]
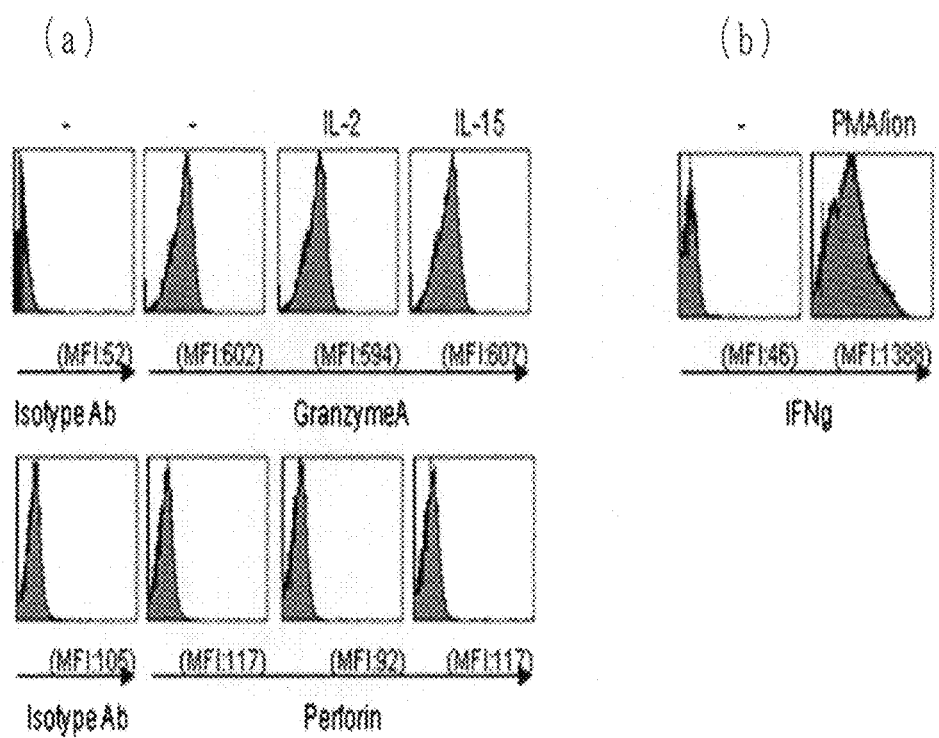
[Figure 16]
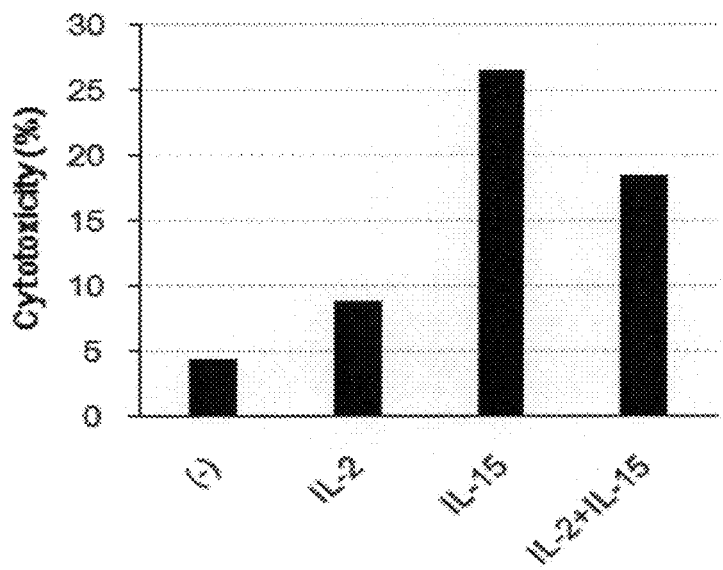

[Figure 17]
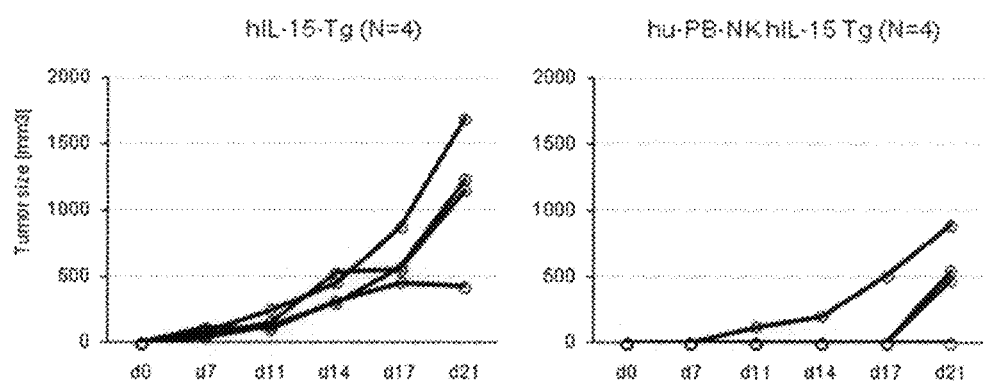
hIL-15 Tg vs. hu-PB-NK hIL-15 Tg
*p<0.05 ated diverse humanized mouse models (see for example, non-patent document 3).
HUMAN IL-15-SECRETING IMMUNODEFICIENT MOUSE

CROSS REFERENCE TO RELATED APPLICATIONS

This application is a National Phase Under 35 USC 371 of International Application No. PCT/JP2016/002112 filed on Apr. 20, 2016, which claims priority to Japanese Application No. 2015-107932 filed May 27, 2015, the contents of which are hereby incorporated by reference in their entirety.

TECHNICAL FIELD

The present invention relates to an immunodeficient mouse which genomic DNA is inserted with a DNA consisting of a nucleotide sequence represented by SEQ ID NO: 1, wherein the immunodeficient mouse is capable of secreting human IL-15, and a h (human) CD56+ cell is detected in vivo for a long period after transplantation of a human peripheral blood-derived human NK cell.

BACKGROUND ART

Humanized immunodeficient mice which enables human cells or human tissues to be analyzed in vivo are regarded as laboratory animals that can be not only utilized as a research tool for drug discovery but expected to contribute to medicine as a useful tool that permits in vivo basic research such as analysis on the differentiation or functions of human cells by the transplantation of the human cells. Thus, an attempt has been made to develop more useful humanized immunodeficient mice over long years.

In 1962, nude mice deficient in thymus-derived T cells due to a lack of the thymus were found as immunodeficient mice. The mice had other immune cells, and normal human cells failed to be engrafted in the mice, though some human cancer cells were successfully engrafted. In 1980, Melvin Bosma et al. found immunodeficient SCID mice which were natural mutants of mice of the C.B-17 strain and exhibited severe combined immunodeficiency (SCID) mutation (see for example, non-patent document 1). The scid mutation takes an autosomal recessive mode of inheritance. The SCID mice achieved some positive results in such a way that the human fetal thymus could be transplanted under the renal capsule of the mice owing to the absence of T cells and B cells. However, the SCID mice did not improve the rate of human cell engraftment to an expected level.

In around 1980, Makino also found female individuals that manifested polyuria and strong positivity to urinary sugar among mice with cataract, and established mice designated as NOD (non-obese diabetes) mice because the symptoms thereof were similar to those of human type 1 diabetes mellitus (insulin-dependent diabetes mellitus) (see for example, non-patent document 2). NOD/scid mice which permitted engraftment of human cells at a rate higher than that of the SCID mice were developed by mating the NOD mice with the SCID mice. The NOD/scid mice exhibited decline in complement activity, macrophage functions, natural killer (NK) cell activity, etc. derived from the NOD strain, and did not reject transplanted human hematopoietic stem cells. However, problems were pointed out, such as engraftment efficiency that was not high, and the short lifespan of the mice.

Furthermore, the present inventors developed NOD/SCID/γc$^{null}$ mice (also simply referred to as "NOG mice") which lack both of functional T cell and B cell, exhibit decline in macrophage function, deletion of NK cell or NK activity, and decline in dendritic cell function, and have excellent engraftment of heterologous cell, by backcrossing C.B-17-scid mice with NOD mice and backcrossing the resulting mice with interleukin 2 receptor γ chain gene-knockout mice (see for example, patent document 1). The NOG mice reportedly have much higher engraftment of human cells or tissues than that of conventional mice, enable transplanted human stem cells to differentiate even into mature cells, and are useful in the generation of diverse humanized mouse models (see for example, non-patent document 3).

On the other hand, NK cells are regarded as one type of cytotoxic lymphocyte that works as a major factor for innate immunity. The NK cells can damage tumor cells or virally infected cells without antigen sensitization and have the property of expressing surface antigens including CD56. However, it has been reported that, in the NOG mice, efficiency of differentiation of transplanted cord blood-derived hematopoietic stem cells into human NK cells were low, and human NK cells were maintained only for a short period even when peripheral blood-derived human mature NK cells are transplanted.

PRIOR ART DOCUMENTS

Patent Documents

Patent document 1: Japanese Patent No. 3753321

Non-Patent Documents

Non-patent document 1: Nature. 301, 527-530, 1983
Non-patent document 2: Jikken Dobutsu. 29: 1-13, 1980
Non-patent document 3: Blood, 100, no. 9, 3175-3182, 2002

SUMMARY OF THE INVENTION

Object to be Solved by the Invention

An object of the present invention is to provide a mouse that enables the functions of human NK cells to be studied.

Means to Solve the Object

The present inventors generated NOD-scid, IL-2rγ$^{null}$-hIL-2 Tg mice by inserting a gene region comprising DNA encoding a human interleukin 2 (hIL-2) signal peptide and hIL-2 protein to genomic DNA of NOD-IL2rγ$^{null}$ mice, and mating the resulting mice with NOG mouse. The present inventors confirmed that in the mice thus prepared, mature human NK cells positive to hCD56 differentiated and proliferated in vivo by the transplantation of human cord blood-derived hematopoietic stem cells (Katano et al., J. Immunol. Feb. 23, 2015, 1401323), whereas human NK-like cells positive to hCD56 hardly proliferated when human peripheral blood was transplanted.

The report (J. Immunol. 1998; 160; 4418-4426) states that when COS cells were transfected with a DNA comprising a sequence in which a sequence encoding the hIL-2 signal peptide was positioned upstream of DNA sequence encoding hIL-15 protein, and allowed to express a hIL-2 signal peptide-hIL-15 fusion protein, the amount of extracellularly secreted hIL-15 protein reached 15 times to 20 times as compared with the case of producing the hIL-15 protein using a DNA comprising a sequence in which a sequence encoding a hIL-15 signal peptide was positioned upstream of a DNA sequence encoding hIL-15.

The present inventors have generated NOD-scid, IL-2rγ$^{null}$-hIL-15 Tg mice by inserting a DNA consisting of a nucleotide sequence represented by SEQ ID NO: 1, which is a gene region comprising DNA in which a cDNA sequence encoding interleukin 15 (IL-15) is operably ligated to a cDNA sequence encoding the signal peptide of human interleukin 2 (IL-2), to the cDNA of immunodeficient mice known in the art, and transplanted cord blood-derived human hematopoietic stem cells to the mice. As a result, the present inventors have confirmed that human CD56$^+$ NK cells differentiate and proliferate, as in the results of the NOD-scid, IL-2rγ$^{null}$-hIL-2 Tg mice.

The present inventors have further continued studies and transplanted human peripheral blood-derived hCD56$^+$ NK cells to the NOD-scid, IL-2rγ$^{null}$-hIL-15 Tg mice. As a result, surprisingly, the number of cells positive to hCD56 increased gradually, and after a lapse of 5 weeks after the transplantation, exhibited a peak value of the concentration as very high as 8000 cells/μL in the mouse blood. Although the number of cells positive to hCD56 then decreased gradually, it has been confirmed that hCD56$^+$ cells having a concentration sufficient for conducting in vivo study on human mature NK cells are detected in the blood of the mouse of the present invention for at least 6 months after the transplantation. The present inventors have further confirmed that the NOD-scid, IL-2rγ$^{null}$-hIL-15 Tg mice suppress growth of human tumor not only in vitro but in vivo after transplantation of human peripheral blood-derived hCD56$^+$ NK cells. On the basis of these findings, the present invention has been completed.

Specifically, the present invention is as follows:

[1] An immunodeficient mouse which genomic DNA is inserted with a DNA consisting of a nucleotide sequence represented by SEQ ID NO: 1, wherein the immunodeficient mouse is capable of secreting human IL-15, and a hCD56$^+$ cell is detected in vivo for a long period after transplantation of a human peripheral blood-derived human NK cell.

[2] The immunodeficient mouse according to [1], wherein the hCD56$^+$ cell is a hCD56$^+$ hCD16$^+$ cell which is further positive to hCD16.

[3] The immunodeficient mouse according to [1] or [2], wherein the hCD56$^+$ cell is a cell that is detected in a spleen, a liver, and/or a lung but is not detected in bone marrow.

[4] The immunodeficient mouse according to any one of [1] to [3], wherein the hCD56$^+$ cell is a cell positive to hNKG2A, hNKG2C, hNKG2D, hCD94, hNKp30, hNKp46, hNKp44, hNKp80, hCD57, hCD158a/h (KIR), hCD158b (KIR), hCD158d (KIR), hCD158e (KIR), or hCD158f (KIR) as a cell surface molecule.

[5] The immunodeficient mouse according to any one of [1] to [4], wherein the immunodeficient mouse is capable of suppressing growth of human tumor in vitro in the presence of a cytokine after transplantation of a human peripheral blood-derived human NK cell.

[6] The immunodeficient mouse according to [5], wherein the cytokine is hIL-15.

[7] The immunodeficient mouse according to any one of [1] to [6], wherein the immunodeficient mouse is capable of suppressing growth of human tumor in vivo after transplantation of a human peripheral blood-derived human NK cell.

[8] A method for generating a NOD-scid, IL-2rγ$^{null}$-hIL-15 Tg mouse, comprising the following steps (1) to (7) sequentially:

(1) introducing a DNA comprising a nucleotide sequence represented by SEQ ID NO: 1 to a vector comprising a region necessary for inserting a DNA consisting of the nucleotide sequence represented by SEQ ID NO: 1 to a mouse genomic DNA, thereby generating a vector for DNA preparation for injection into mouse fertilized eggs having the DNA comprising the nucleotide sequence represented by SEQ ID NO: 1;

(1-1) optionally preparing a DNA fragment for injection into fertilized eggs wherein the DNA fragment comprises the DNA consisting of the nucleotide sequence represented by SEQ ID NO: 1, and a region necessary for insertion of the DNA comprising the nucleotide sequence represented by SEQ ID NO: 1 to mouse genomic DNA;

(2) injecting the vector generated in the step (1) and/or the vector fragment prepared in the step (1-1) into a fertilized egg of an interleukin 2 receptor γ chain gene (IL-2Rγ)-knockout mouse, thereby generating an injected-fertilized egg;

(3) culturing the injected-fertilized egg generated in the step (2), thereby generating a newborn mouse;

(4) determining whether or not the DNA comprising the nucleotide sequence represented by SEQ ID NO: 1 is inserted in genomic DNA of a NOD-IL-2rγ$^{null}$ mouse among the mouse generated in the step (3);

(5) determining whether or not the mouse determined in the step (4) that the DNA comprising the nucleotide sequence represented by SEQ ID NO: 1 is inserted in genomic DNA of the NOD-IL-2rγ$^{null}$ mouse secretes hIL-15, thereby selecting a hIL-15-secreting mouse as a NOD-IL-2rγ$^{null}$-hIL-15 Tg mouse;

(6) mating the NOD-IL-2rγ$^{null}$-hIL-15 Tg mouse with a NOG mouse, thereby generating a NOD-scid, IL-2rγ$^{null}$-hIL-15 Tg mouse containing scid mutation; and (7) mating the NOD-scid, IL-2rγ$^{null}$-hIL-15 Tg mouse with a NOG mouse, thereby generating a NOD-scid, IL-2rγ$^{null}$-hIL-15 Tg mouse and a NOG mouse at a ratio of 1:1.

Effect of the Invention

According to the present invention, human peripheral blood-derived NK cell transplanted in the mouse of the present invention can be maintained for a very long period in the mouse, and the functions of human NK cell can be analyzed in vivo over a long period.

BRIEF DESCRIPTION OF DRAWINGS

FIG. 1(a) shows the schematic representation of a pCMVβ vector, and FIG. 1(b) shows the schematic representation of a vector for DNA preparation for injection into fertilized eggs.

FIG. 2 shows the schematic representation of a DNA fragment for injection into fertilized eggs.

FIG. 3 shows a hIL-15 concentration in the plasma of NOG-hIL-15 Tg mice.

FIG. 4(a) shows the respective amounts (/μL) of hCD45$^+$ cells, hCD19$^+$ cells, and hCD56$^+$ cells in mononuclear cells (MNC), and FIG. 4(b) shows the ratio (%) of the number of hCD45$^+$ cells, hCD19$^+$ cells, and hCD56$^+$ cells to mononuclear cells, in stem cell-transplanted mice.

FIG. 5 shows flow cytometry analysis results of immune cells obtained from each of the bone marrow, the spleen, and the peripheral blood of stem cell-transplanted mice.

FIG. 6 shows results of analyzing the expression of human NK cell-specific receptors by flow cytometry analysis on human NK cells in stem cell-transplanted mice.

FIG. 7 shows flow cytometry analysis results of the ability of human hematopoietic stem cell-derived NK cells to secrete cytotoxic granules. FIG. 7(a) shows the results of the expression of granzyme A and perforin, and FIG. 7(b) shows the results of hIFNγ expression.

FIG. 8 shows flow cytometry analysis results of the peripheral blood of peripheral blood-transplanted hIL-15 mice.

FIG. 9(a) shows the ratio (%) of the number of hCD56+ cells to mononuclear cells (MNC), and FIG. 9(b) shows the ratio (%) of the number of CD3+ T cells to mononuclear cells (MNC), in peripheral blood-transplanted mice. FIG. 9(c) shows the number of hCD56+ cells (/μL) in the blood of peripheral blood-transplanted hIL-15 mice. FIG. 9(d) shows the number of hCD56+ cells (/μL) in the blood of peripheral blood-transplanted non-Tg mice.

FIG. 10 is a graph showing change in two types of human mature NK cell sub-populations in the peripheral blood of peripheral blood-transplanted hIL-15 mice.

FIG. 11 shows flow cytometry analysis results of the peripheral blood of frozen peripheral blood hIL-15 mice.

FIG. 12 is a graph showing fluctuation in two types of human mature NK cell sub-populations in the peripheral blood of frozen peripheral blood hIL-15 mice.

FIG. 13 shows flow cytometry analysis results of the distribution of human NK cells in each tissue of peripheral blood-transplanted hIL-15 mice.

FIG. 14 shows flow cytometry analysis results of cell surface molecules of human NK cells isolated from the spleen of peripheral blood-transplanted hIL-15 mice.

FIG. 15 shows flow cytometry analysis results of the ability of human peripheral blood-derived NK cells to secrete cytotoxic granules. FIG. 15(a) shows the results of the expression of granzyme A and perforin, and FIG. 15(b) shows the results of hIFNγ expression.

FIG. 16 is a graph showing the ability of hCD56+ cells isolated from peripheral blood-transplanted hIL-15 mice to suppress tumor growth in vitro.

FIG. 17 is a graph showing the in vivo cytotoxic activity against human tumor subcutaneously transplanted in peripheral blood-transplanted hIL-15 mice.

MODE OF CARRYING OUT THE INVENTION

The immunodeficient mouse of the present invention is not particularly limited as long as the immunodeficient mouse which genomic DNA is inserted with a DNA consisting of a nucleotide sequence represented by SEQ ID NO: 1, wherein the immunodeficient mouse is capable of secreting human IL-15 and can maintain a transplanted human NK cell in vivo for a long period. The human IL-15 is one type of human cytokine protein produced by human peripheral blood mononuclear cell. The nucleotide sequence represented by SEQ ID NO: 1 is the nucleotide sequence of a hIL-2SP cDNA/hIL-15 cDNA ligation product in which cDNA encoding interleukin 15 protein (hIL-15) (hereinafter, also referred to as "hIL-15 cDNA") is operably ligated to cDNA encoding a human interleukin 2 (hIL-2) signal peptide (hereinafter, also referred to as "hIL-2SP cDNA").

Examples of the method for determining whether or not the DNA consisting of the nucleotide sequence represented by SEQ ID NO: 1 is inserted in genomic DNA of the mouse can include a method of making confirmation by PCR using a primer set appropriate for detecting the DNA consisting of the nucleotide sequence represented by SEQ ID NO: 1, and a method of making confirmation by Southern blot analysis, as to the genomic DNA extracted from the tissue of the mouse.

Examples of the method for determining whether or not the immunodeficient mouse of the present invention secretes human IL-15 can include a method of determining whether or not human IL-15 is detected in body fluid extracts of lymph or blood (e.g., serum and plasma), organ extracts, or the like from the mouse of the present invention by an immunological assay method using an antibody specifically recognizing hIL-15. Examples of the immunological assay method can include a method of making confirmation by immunohistochemical staining, ELISA, EIA, RIA, or Western blot analysis. Specific examples thereof can include a method of adding an anticoagulant to harvested mouse peripheral blood and determining whether or not human IL-15 is detected in a plasma fraction using a commercially available ELISA kit including an anti-hIL-15 antibody.

Examples of the human peripheral blood-derived human NK cell according to the present invention can include human NK cell contained in human peripheral blood, human NK cell isolated from human peripheral blood, human NK cell in vitro cultured using human peripheral blood, human NK cell contained in human peripheral blood cryopreserved and then thawed, human NK cell isolated from human peripheral blood followed by cryopreserving and then thawing, and human NK cell in vitro cultured using human peripheral blood followed by cryopreserving and then thawing.

Examples of the method for transplanting the human NK cell to the immunodeficient mouse of the present invention can include a method of irradiating the immunodeficient mouse with radiation, such as X-ray, which destroys the environment within the bone marrow in order to improve the engraftment capability of transplanted xenogeneic cell, and transplanting human peripheral blood-derived hCD56+ NK cell to the immunodeficient mouse thus irradiated with radiation. Preferred examples of the intensity of the radiation for irradiation can include 1.5 to 3.5 Gy. The time of the transplantation is preferably within 24 hours after the irradiation with radiation. The number of NK cell grafts to be transplanted can be preferably 0.2 to 10×10$^6$ cells, preferably 0.5 to 3×10$^6$ cells, more preferably 1 to 2×10$^6$ cells.

The method for confirming whether or not the hCD56+ cell is detected in vivo in the immunodeficient mouse of the present invention can employ a method known in the art. Examples thereof can include a method of confirming, by flow cytometry analysis, whether or not cell in the blood of the immunodeficient mouse of the present invention or cells isolated from the blood of the immunodeficient mouse of the present invention are hCD56+ cells which are positive to hCD56.

Specifically, in the flow cytometry analysis, the hCD56+ cells can be present at 1% or more, preferably 3% or more, more preferably 5% or more, further preferably 10% or more, of mononuclear cells, or the hCD56+ cells can be present at at least 40 cells/μL in blood.

Examples of the conditions for enhancing the phenotypic identity of the hCD56+ cell according to the present invention to NK cell matured in a human in vivo can include the case where both of human CD56+ CD16+ cell and human CD56+ CD16− cell are detected in blood, a spleen, a liver, and/or a lung, whereas neither the human CD56+ CD16+ cell nor the human CD56+ CD16− cell are detected in bone marrow. In the present invention, the phrase "hCD56+ cell is detected in a mouse organ or tissue such as a spleen, a liver, a lung, or blood" is also expressed as the phrase "hCD56+ cell is engrafted".

Examples of the additional conditions for complementing the phenotypic identity of the hCD56+ cell according to the present invention to NK cell matured in a human in vivo can include the case where the cell is positive to (expresses) some of antigens such as hNKG2A, hNKG2C, hNKG2D, hCD94, hNKp30, hNKp46, hNKp44, hNKp80, hCD57, hCD158a/h (killer immunoglobulin-like receptor: KIR), hCD158b (KIR), hCD158d (KIR), hCD158e (KIR), and hCD158f (KIR) known as cell surface molecules specific for mature NK cell in human tissues, and can preferably include the case where the cell exhibits the expression of all of hNKG2A, hNKG2C, hNKG2D, hCD94, hNKp30, hNKp46, hNKp44, hNKp80, hCD57, hCD158a/h (KIR), hCD158b (KIR), hCD158d (KIR), hCD158e (KIR), and hCD158f (KIR), as in NK cell (donor) before transplantation.

Examples of the further additional conditions for enhancing the phenotypic identity of the hCD56$^+$ cell according to the present invention to NK cell matured in a human in vivo can include the case where the cell is positive to hNKp46 known as a member of the natural cytotoxicity receptor (NCR) family which induces the cytotoxic activity of NK cell, and the case where the cell is positive to granzyme A.

Examples of the method for confirming whether or not the immunodeficient mouse of the present invention is capable of suppressing growth of human tumor in vitro after transplantation of a human peripheral blood-derived human NK cell can include a method of culturing hCD56$^+$ NK cell isolated from the spleen in the presence of a cytokine, then coculturing the cultured cell with target human tumor cell, and evaluating the culture supernatant for the degree of coloration attributed to the coupled enzyme reaction of a dead cell-derived cytoplasmic enzyme LDH with a reaction substrate, thereby measuring cytotoxic activity (cytotoxicity (%)). Examples of the cytokine can include human IL-2, human IL-15, and a mixed composition of human IL-2 and human IL-15. Human IL-15 is preferred.

Examples of the method for confirming whether or not the immunodeficient mouse of the present invention is capable of suppressing growth of human tumor in vivo after transplantation of a human peripheral blood-derived human NK cell can include a method of further transplanting a NK-sensitive human tumor cell line after transplantation of a human peripheral blood-derived human NK cell, measuring a tumor size over time, and determining whether or not the tumor size is reduced.

Examples of the long period for which the hCD56$^+$ cell is detected in vivo can include 8 weeks or longer. The long period is preferably 12 weeks or longer, more preferably 16 weeks or longer, further preferably 20 weeks or longer, particularly preferably 24 weeks or longer.

Preferred examples of the immunodeficient mouse of the present invention can include a NOD-scid, IL-2rγ$^{null}$-hIL-15 Tg mouse. Examples of the method for generating the immunodeficient mouse according to the present invention can include, but are not particularly limited to, a method for generating the NOD-scid, IL-2rγ$^{null}$-hIL-15 Tg mouse, comprising the following steps (1) to (7) sequentially:

(1) introducing a DNA comprising a nucleotide sequence represented by SEQ ID NO: 1 to a vector comprising a region necessary for inserting of a DNA consisting of the nucleotide sequence represented by SEQ ID NO: 1 to mouse genomic DNA, thereby generating a vector for DNA preparation for injection into mouse fertilized eggs having the DNA comprising the nucleotide sequence represented by SEQ ID NO: 1;

(1-1) optionally preparing a DNA fragment for injection into fertilized eggs wherein the DNA fragment comprises the DNA consisting of the nucleotide sequence represented by SEQ ID NO: 1, and a region necessary for insertion of the DNA comprising the nucleotide sequence represented by SEQ ID NO: 1 to mouse genomic DNA;

(2) injecting the vector generated in the step (1) and/or the vector fragment prepared in the step (1-1) into a fertilized egg of an interleukin 2 receptor γ chain gene (IL-2Rγ)-knockout mouse, thereby generating an injected-fertilized egg;

(3) culturing the injected-fertilized egg generated in the step (2), thereby generating a newborn mouse;

(4) determining whether or not the DNA comprising the nucleotide sequence represented by SEQ ID NO: 1 is inserted in genomic DNA of a NOD-IL-2rγ$^{null}$ mouse among the mouse generated in the step (3);

(5) determining whether or not the mouse determined in the step (4) that the DNA comprising the nucleotide sequence represented by SEQ ID NO: 1 is inserted in genomic DNA of the NOD-IL-2rγ$^{null}$ mouse secretes hIL-15, thereby selecting a hIL-15-secreting mouse as a NOD-IL-2rγ$^{null}$-hIL-15 Tg mouse;

(6) mating the NOD-IL-2rγ$^{null}$-hIL-15 Tg mouse with a NOG (NOD-scid, IL-2rγ$^{null}$) mouse, thereby generating a NOD-scid, IL-2rγ$^{null}$-hIL-15 Tg mouse containing scid mutation; and (7) mating the NOD-scid, IL-2rγ$^{null}$-hIL-15 Tg mouse with a NOG mouse, thereby generating a NOD-scid, IL-2rγ$^{null}$-hIL-15 Tg mouse and a NOG mouse at a ratio of 1:1.

In the step (1), examples of the insert region necessary for insertion of DNA consisting of the nucleotide sequence represented by SEQ ID NO: 1 to a mouse genomic DNA can include a region comprising a promoter operable in mouse cell, such as cytomegalovirus promoter (pCMV-IE), SV40 SS/SA, and SV40 polyA. Examples of the expression vector comprising such an insert region can include pCMVβ.

Examples of the method for generating the vector for DNA preparation for injection into mouse fertilized eggs comprising the DNA consisting of the nucleotide sequence represented by SEQ ID NO: 1 can include a method using a gene recombination technique known in the art, and can specifically include a method of cleaving pCMV-LacZ with a restriction enzyme NotI, and replacing DNA encoding β-galactosidase with the DNA consisting of the nucleotide sequence represented by SEQ ID NO: 1.

In the step (1-1), examples of the method for generating the DNA fragment for injection into fertilized eggs can include a method using a gene recombination technique known in the art, and can specifically include a method of cleaving the vector for DNA preparation for injection into mouse fertilized eggs having the DNA comprising the nucleotide sequence represented by SEQ ID NO: 1 with a restriction enzyme PvuII, and purifying a vector fragment having the DNA consisting of the nucleotide sequence represented by SEQ ID NO: 1 and the DNA comprising the insert region.

In the step (2), the method for generating the injected-fertilized egg is not particularly limited as long as the method can inject the vector for DNA preparation for injection into mouse fertilized eggs or the DNA fragment for injection into fertilized eggs into a mouse fertilized egg. Examples thereof can include a method by microinjection, electroporation, and a viral vector method. Examples of the interleukin 2 receptor γ chain gene (IL-2Rγ)-knockout mouse can preferably include a NOD-IL-2rγ$^{null}$ mouse.

In the step (3), the method for culturing the injected-fertilized egg is not particularly limited as long as the method can produce a newborn mouse. Examples thereof can include a method of culturing the injected fertilized egg ex vivo at 37° C. for 18 to 24 hours, then transplanting or implanting the fertilized egg to the uterus of a foster mother, and performing cesarean section immediately before delivery to obtain a newborn mouse. Preferably, such a newborn mouse is further subjected to cross fostering to prepare mouse offspring.

In the step (4), examples of the method for determining whether or not the nucleotide sequence represented by SEQ ID NO: 1 is inserted in genomic DNA of the newborn mouse or the mouse offspring can include a method of confirming, by PCR, whether or not the nucleotide sequence represented by SEQ ID NO: 1 is inserted in the genomic DNA extracted from the tissue of the mouse when the mouse becomes 3 to 4 weeks or older in age.

In the step (5), examples of the method for determining whether or not the mouse determined in the step (4) that the DNA comprising the nucleotide sequence represented by SEQ ID NO: 1 is inserted in genomic DNA of the NOD-IL-2rγ$^{null}$ mouse secretes hIL-15 can include the immunological assay method described above using an antibody specifically recognizing hIL-15.

In the step (6), the method for generating the NOD-scid, IL-2rγ$^{null}$-hIL-15 Tg mouse is not particularly limited as long as the method can introduce scid mutation to the mouse selected as the NOD-IL-2rγ$^{null}$-hIL-15 Tg mouse. Specific examples thereof can include a method of mating the NOD-IL-2rγ$^{null}$-hIL-15 Tg mouse with a NOG (NOD-scid, IL-2 rγ$^{null}$) mouse.

In the step (7), the NOD-scid, IL-2rγ$^{null}$-hIL-15 Tg mouse can be mated with a NOG mouse to obtain a NOD-scid, IL-2rγ$^{null}$-hIL-15 Tg mouse and a NOG mouse at a ratio of 1:1.

Hereinafter, the present invention will be described more specifically with reference to Examples. However, the technical scope of the present invention is not limited by these examples.

EXAMPLES

Example 1

[Generation of NOD-Scid, IL-2rγ$^{null}$-hIL-15 Tg Mouse Producing IL-15]
(Outline)

According to the guidance approved by the animal experiment committee of Central Institute for Experimental Animals (hereinafter, also referred to as "CIEA"), NOD-scid, IL-2rγ$^{null}$-hIL-15 Tg mice were generated as transgenic mice secreting human IL-15 by using NOD-IL-2rγ$^{null}$ mice and NOD-scid, IL-2rγ$^{null}$ mice (hereinafter, also referred to as "NOG mice"). These mice are specially controlled in the SPF animal facilities of CIEA and can be distributed under predetermined conditions.

(Preparation of DNA for Injection into Fertilized Egg)

A reporter vector pCMVβ for mammals (manufactured by Invitrogen Corp.) (see FIG. 1(a)) was used to construct a vector for DNA preparation for injection into fertilized eggs in which SV40 SD/SV DNA, DNA consisting of the nucleotide sequence represented by SEQ ID NO: 1 (hIL-2SP cDNA/hIL-15 cDNA ligation product), and polyA sequence DNA were integrated in order downstream of cytomegalovirus promoter (pCMV-IE) DNA. Specifically, the pCMV-LacZ was cleaved with a restriction enzyme NotI, and a gene encoding β-galactosidase was replaced with a DNA comprising the nucleotide sequence of the hIL-2SP cDNA/hIL-15 cDNA ligation product determined with reference to GenBank (Accession Nos: hIL-2 (NM_000586) and hIL-15 (NM_000585 or BC100962).

Specifically, pCMVβ was treated with a restriction enzyme NotI to remove a β-galactosidase gene sequence moiety. The hIL-2SP cDNA/hIL-15 cDNA ligation product cleaved with NotI was inserted thereinto. The hIL-2SP cDNA/hIL-15 cDNA ligation product was separately prepared. Specifically, from cDNA generated from healthy human peripheral blood mononuclear cell, a hIL-2SP moiety was amplified using Primer A: ATAGCGGCCGCTCACAGTAACCTCAACTCCTGCAA (SEQ ID NO: 2) and Primer B: ATCACTAGTTGCACTGTTTGTGACAAGTGC (SEQ ID NO: 3), and a hIL-15MP moiety was amplified using Primer C: GGGACTAGTAACTGGGTGAATGTAATAAGTG (SEQ ID NO: 4) and Primer D: CAACTAGTTCACTTGTCACGTCGTCCTTGTAGTCAGAAGTGTTGATGAA (SEQ ID NO: 5). Each amplified fragment was inserted to a PCR2.1 vector(R) (manufactured by Invitrogen Corp.). Then, the hIL-2SP moiety was cleaved with NotI and inserted to the pCMVβ free from the β-galactosidase gene sequence moiety. Then, a region comprising the human IL-15 cDNA moiety was obtained by cleavage with SpeI and inserted to the vector. FIG. 1(b) shows the schematic representation of the constructed vector for DNA preparation for injection into fertilized eggs.

The vector for DNA preparation for injection into fertilized eggs was cleaved with a restriction enzyme PvuII. A vector fragment comprising a region necessary for injection into fertilized eggs was purified to prepare an 1840 bp DNA fragment for injection into fertilized eggs (see FIG. 2). The sequence of the DNA fragment for injection into fertilized eggs is shown in SEQ ID NO: 6.

(Generation of NOD-IL-2rγ$^{null}$-hIL-15 Tg Mouse)

The DNA for injection into fertilized eggs was adjusted to a concentration of 1.5 ng/mL and microinjected into 123 pronuclear fertilized eggs of NOD-IL-2rγ$^{null}$ mice using an inverted microscope with a micromanipulator (manufactured by Leica Camera AG).

After culture of the pronuclear fertilized eggs in which the DNA for injection into fertilized eggs was microinjected, 63 two-celled embryos confirmed as fertilized eggs that normally reached the 2-cell stage were transplanted to the oviducts of recipient mother mice. Cesarean section was performed immediately before delivery to obtain newborn mice, which were further subjected to cross fostering to obtain 24 mouse offsprings.

(Gene Analysis)

When the mouse offsprings became 3 to 4 weeks old, a piece of tissue was harvested from 1 to 2 mm of the tail tip of each mouse offspring. The genomic DNA extracted therefrom using an automatic DNA extraction apparatus (manufactured by Toyobo Co., Ltd.) was subjected to PCR using the following primer set under the following conditions to confirm whether or not the nucleotide sequence represented by SEQ ID NO: 1 was inserted in genomic DNA of each offspring.

```
(Primer)
IL2SPS1:
(forward primer)
                                      (SEQ ID NO: 7)
5'-ATAGCGGCCGCTCACAGTAACCTCAACTCCTGCCA-3'

IL15mpAS3:
(reverse primer)
                                      (SEQ ID NO: 8)
5'-CAACTAGTTCACTTGTCATCGTCGTCCTTGTAGTCAGAA-3'
```

(PCR Reaction Solution)
Solution A:
2.5 μL of ×10 buffer for Ex-taq
2 μL of dNTP mix
1.25 μL of IL2SPS1 (5 μM)
1.25 μL of IL15mpAS3 (5 μM)
0.125 μL of Ex-taq
6.875 μL of DW
Solution B:
8.5 μL of DW
1.5 μL of genomic DNA Solution A and solution B were mixed to prepare a PCR reaction solution.
(PCR Amplification Conditions)

24 μL of the PCR reaction solution was used in amplification treatment under conditions involving heat treatment at 94° C. for 3 minutes; 35 cycles each involving 94° C. for 30 seconds, 60° C. for 30 seconds, and 72° C. for 1 minute; and subsequent heat treatment at 72° C. for 2 minutes. The PCR product obtained by the PCR was subjected to electrophoresis in 2% agarose gel. The presence or absence of an amplification product band at or around 480 bp was confirmed to determine whether or not the DNA comprising the nucleotide sequence represented by SEQ ID NO: 1 was inserted in genomic DNA of each mouse offspring described above.

Blood was collected from the mouse offsprings confirmed in the gene analysis to have an insert of the DNA comprising the nucleotide sequence represented by SEQ ID NO: 1 in the genomic DNA. The presence or absence of secretion of hIL-15 into serum/plasma fractions was confirmed by ELISA using BioLegend Human IL-15 kit (cat No. 435108). The mice confirmed to secrete hIL-15 were designated as NOD-IL-2rγ$^{null}$-hIL-15 Tg mice.
(Generation of NOD-Scid, IL-2rγ$^{null}$-hIL-15 Tg Mouse)

The NOD-IL-2rγ$^{null}$-hIL-15 Tg mice (female) were mated with NOD-scid, IL-2rγ$^{null}$ mice (hereinafter, also referred to as "NOG mice") (male) so that scid mutation to cause deficiency in T cell and B cell serving as major cells in charge of the immune system was further introduced to the NOD-IL-2rγ$^{null}$-hIL-15 Tg mice to generate NOD-scid, IL-2rγ$^{null}$-hIL-15 Tg mice (hereinafter, also referred to as "NOG-hIL-15 Tg mice").

The NOG-hIL-15 Tg mice were mated with NOG mice to obtain NOG-hIL-15 Tg mice and NOG mice at a ratio of 1:1. In Example 2 or later, the NOG-hIL-15 Tg mice were studied by using the NOG mice (hereinafter, also referred to as "non-Tg mice") as negative controls having no insert of the gene having the nucleotide sequence represented by SEQ ID NO: 1 in the genomic DNA.

Example 2

[Study on NOG-hIL-15 Tg Mouse]
(hIL-15 Concentration in Plasma)

The hIL-15 concentration in the plasma of the NOG-hIL-15 Tg mice was measured. Peripheral blood was collected from 4 to 6 weeks old mouse individuals under anesthesia using heparin (Novo-heparin, manufactured by Mochida Pharmaceutical Co., Ltd.). The hIL-15 concentration in the plasma was measured using the ELISA kit described above. The results are shown in FIG. 3.
(Results)

As is evident from FIG. 3, the hIL-15 concentration in the plasma of the NOG-hIL-15 Tg mice ("hIL-15 Tg" in the figure) (N=126) was 47.7±27.5 pg/mL, whereas the hIL-15 concentration in the plasma of the non-Tg mice was 1.3±1.5 pg/mL. Thus, the NOG-hIL-15 Tg mice having the insert in the genomic DNA had a remarkably higher hIL-15 concentration than that of the NOG mice, demonstrating that hIL-15 systemically produced by the gene having the nucleotide sequence represented by SEQ ID NO: 1 inserted in the genomic DNA was secreted into blood.

Example 3

[Study on Ability of Human Cell to Differentiate in Human Cord Blood-Derived CD34$^+$ Hematopoietic Stem Cell-Transplanted NOG-hIL-15 Tg Mouse]
(Flow Cytometry Measurement Procedure)

The study using flow cytometry in Example 3 or later was conducted by the following procedures: assuming that the hCD56$^+$ cells were human NK cells, analysis was conducted using antibodies suitable for each study item. Specifically, the cells were stained at 4° C. for 30 minutes in the dark, then washed with a FACS buffer solution (PBS containing 1% FBS and 0.1% NaN$_3$), and resuspended in a FACS buffer solution containing propidium iodide, followed by flow cytometry measurement. The flow cytometry measurement was performed using a BD FACSCanto™ flow cytometer (manufactured by Becton, Dickinson and Company). The data was analyzed using FACSDiva software (ver. 6.1.3) (manufactured by Becton, Dickinson and Company). The absolute value of the number of cells was calculated using Flow-Count (manufactured by Beckman Coulter Inc.) according to the instruction manual.
(Antibody)

The antibodies used were specifically as follows.
Anti-hCD3 antibody: anti-human CD3-FITC (manufactured by BioLegend, Inc.) and anti-human CD3-PE (manufactured by BioLegend, Inc.),
Anti-hCD16 antibody: anti-human CD16-FITC (manufactured by BioLegend, Inc.),
Anti-hCD19 antibody: anti-CD19 (manufactured by BioLegend, Inc.),
Anti-hCD33 antibody: anti-human CD33-FITC (manufactured by BD Biosciences),
Anti-hCD45 antibody: anti-human CD45-allophycocyanin-Cy7 (manufactured by BioLegend, Inc.),
Anti-hCD56 antibody: anti-human CD56-PE (manufactured by BioLegend, Inc.),
Anti-hCD57 antibody: anti-CD57 (manufactured by BioLegend, Inc.),
Anti-NKG2A antibody: anti-human CD159a (NKG2A)-PE (manufactured by Beckman Coulter Inc.),
Anti-NKG2C antibody: Alexa Fluor 488-conjugated anti-human NK group 2 membrane C (manufactured by R&D Systems, Inc.),
Anti-NKG2D antibody: anti-NKG2D (manufactured by BioLegend, Inc.),
Anti-hCD94 antibody: anti-CD94 (manufactured by BioLegend, Inc.),
Anti-hNKp30 antibody: anti-NKp30 (manufactured by BioLegend, Inc.),
Anti-hNKp46 antibody: anti-NKp46 (manufactured by BioLegend, Inc.),
Anti-hNKp44 antibody: anti-NKp44 (manufactured by BioLegend, Inc.),
Anti-hNKp80 antibody: anti-human NKp80-PE (manufactured by Beckman Coulter Inc.),
Anti-hCD158a/h antibody (killer immunoglobulin-like receptor: KIR) (KIR2DL1/S1/S3/S5): FITC-conjugated anti-CD158a/h (manufactured by BioLegend, Inc.), Anti-hCD158b antibody (KIR2DL2/L3, NKAT2): anti-CD158b (manufactured by BioLegend, Inc.),
Anti-hCD158d antibody (KIR2DL4): anti-CD158d (manufactured by BioLegend, Inc.),
Anti-hCD158e antibody (KIR3DL1, NKB1): anti-CD158e (manufactured by BioLegend, Inc.),
Anti-hCD158f antibody (KIR2DL5): anti-CD158f (manufactured by BioLegend, Inc.), and
Anti-mCD45 antibody: anti-mouse CD45-allophycocyanin (manufactured by BioLegend, Inc.)

Example 4

(Generation of Human Cord Blood-Derived hCD34$^+$ Hematopoietic Stem Cell-Transplanted NOG-hIL-15 Tg Mouse)

Human cord blood-derived hCD34$^+$ hematopoietic stem cells were transplanted to the 8 to 12 weeks old adult NOG-hIL-15 Tg mice. The mice were irradiated with 2.5 Gy X-ray. Within 24 hours after the irradiation, 2×10$^4$ human cord blood-derived hCD34$^+$ hematopoietic stem cells were transplanted via the tail vein to generate human cord blood-derived hCD34$^+$ hematopoietic stem cell-transplanted NOG-hIL-15 Tg mice (hereinafter, also referred to as "stem cell-transplanted hIL-15 mice"). Similarly, human cord blood-derived hCD34$^+$ hematopoietic stem cell-transplanted NOG mice (hereinafter, also referred to as "stem cell-transplanted non-Tg mice") were generated and used as negative controls. Also, human cord blood-derived hCD34$^+$ hematopoietic stem cell-transplanted in NOG-hIL-2 Tg mice having an insert of interleukin 2 (hIL-2) signal peptide cDNA in the genomic DNA, which were already confirmed to cause selective differentiation into and proliferation of human NK cells (hereinafter, also referred to as "stem cell-transplanted hIL-2 mice") were used as positive controls.

Example 5

(Study on Ability of Human Cell to Differentiate in Peripheral Blood of Cord Blood-Derived hIL-15 Mouse)

From the 3 types of hCD34$^+$ hematopoietic stem cell-transplanted mice, peripheral blood was collected after a lapse of 4 weeks after the transplantation. Cells in the peripheral blood were stained with respective specific antibodies against an antigen hCD56 serving as a marker for NK cells, an antigen hCD45 serving as a marker for leucocytes, an antigen hCD19 serving as a marker for B cells, and an antigen hCD3 serving as a marker for T cells, followed by flow cytometry measurement to analyze the ratio of human leucocyte chimeras in the mouse blood. FIG. 4(a) shows the amounts (/μL) of human immune cells in mononuclear cells (MNC), and FIG. 4(b) shows the ratio (%) of the number of the cells to mononuclear cells.
(Results 1)

As is evident from FIG. 4(a), hCD56$^+$ cells were largely present in the peripheral blood of the stem cell-transplanted hIL-15 mice and the stem cell-transplanted hIL-2 mice at 4 weeks after the transplantation, demonstrating selective differentiation into and proliferation of human NK cells. On the other hand, hCD56-positive cells were hardly present in the peripheral blood of the stem cell-transplanted non-Tg mice. The presence of hCD19$^+$ cells was approximately 3 cells/μL in the peripheral blood of the stem cell-transplanted hIL-2 mice, and was on the order of 1 to 2 cells/μL in the peripheral blood of the stem cell-transplanted hIL-15 mice and the stem cell-transplanted non-Tg mice. Differentiation into and proliferation of human B cells were hardly observed in any of the mice.
(Results 2)

As is evident from FIG. 4(b), hCD56$^+$ cells were very largely present in the peripheral blood of the stem cell-transplanted hIL-15 mice and the stem cell-transplanted hIL-2 mice at 4 weeks after the transplantation, demonstrating differentiation into and proliferation of human CD56$^+$ NK cells.

Example 6

(Study on Ability of Human Cell to Differentiate in Each Tissue of Stem Cell-Transplanted hIL-15 Mouse)

From the 3 types of hCD34$^+$ hematopoietic stem cell-transplanted test mice, bone marrow, the spleen, and peripheral blood were harvested after a lapse of 6 weeks after the transplantation. Human CD56$^+$ NK cells were isolated and stained with each specific antibody, followed by flow cytometry measurement to analyze the ability of human cells to differentiate in each mouse tissue. The results are shown in FIG. 5.
(Results)

As is evident from FIG. 5, the localization of human NK cells was confirmed in the red boxes indicated as hCD56$^+$ and hCD45$^+$ fractions in all of the bone marrow (BM), the spleen (SPL), and the peripheral blood (PB) of the stem cell-transplanted hIL-15 mice and the stem cell-transplanted hIL-2 mice, whereas the localization of human NK cells was hardly confirmed in the stem cell-transplanted non-Tg mice.

Example 7

(Expression Analysis of Receptor Specific for Human Hematopoietic Stem Cell-Derived NK Cell)

The human NK cells isolated from the spleen of the stem cell-transplanted hIL-15 mice and the stem cell-transplanted hIL-2 mice were stained with respective specific antibodies against an antigen hCD16 reported as a specific cell surface molecule in a subfraction of mature NK cells differentiated in humans in vivo, an antigen hCD57 reported to be expressed in a cell subset having NK activity in human peripheral blood, an antigen hNKG2A reported as a suppressive receptor expressed on NK cell surface, an antigen hNKG2C reported as an active receptor expressed on NK cell surface, and an antigen hNKG2D reported as an active receptor expressed on NK cell surface, followed by flow cytometry measurement to analyze the expression of receptors specific for the human NK cells. Japanese PB-NK cells (human NK cells isolated from the peripheral blood of Japanese donors under informed consent), which were human peripheral blood mature NK cells, were used as positive controls. The results are shown in FIG. 6.
(Results)

As is also evident from FIG. 6, the expression of the antigen hCD16, the antigen hCD57, the antigen hNKG2A, the antigen hNKG2C, and the antigen hNKG2D was confirmed in the NK cells in the peripheral blood in both the stem cell-transplanted hIL-15 Tg mice and the stem cell-transplanted hIL-2 Tg mice. However, the expression patterns thereof differed from the expression patterns in human peripheral blood mature NK cells in that: the expression intensity of the antigen hCD56 was high; and the proportion of the hCD56$^+$ CD16$^-$ fraction was large. These expression patterns of the NK cell-specific antigens were similar to those in hCD56$^+$ CD16$^-$ activated NK cells which increase in the blood of patients who have clinically received IL-2 dosing therapy. Therefore, it was presumed that the human hematopoietic stem cell-derived NK cells differentiated in the stem cell-transplanted hIL-15 mice and the stem cell-transplanted hIL-2 mice were rich in NK cells activated by hIL-15 or hIL-2 within the mice.

Example 8

(Verification of Ability of Human Hematopoietic Stem Cell-Derived NK Cell to Secrete Cytotoxic Granule)

Whether or not the human NK cells isolated from the spleen of the stem cell-transplanted hIL-15 Tg mice and the stem cell-transplanted hIL-2 Tg mice would have the ability to secrete cytotoxic granules and the ability to produce cytokines, was verified. The spleen was harvested from each mouse after a lapse of 6 weeks after the transplantation, followed by cell preparation. Human $CD56^+$ NK cells were isolated, cultured for 20 hours in the presence of Brefeldin A (manufactured by BioLegend, Inc.), and then intracellularly stained with fluorescently labeled antibodies (FITC-anti-hgranzyme A antibody and FITC-anti-perforin antibody (manufactured by BioLegend, Inc.), followed by flow cytometry measurement. The results are shown in FIG. 7(a). Also, the isolated human $CD56^+$ NK cells were cultured in the presence of PMA/ionomycin and then intracellularly stained with a fluorescently labeled antibody PE-anti-hIFNg antibody (manufactured by BioLegend, Inc.), followed by flow cytometry measurement. The results are shown in FIG. 7(b).

(Results)

As is evident from FIG. 7(a), the expression of granzyme A (cytotoxic granules) comparable to results of mature NK cells differentiated in humans in vivo (data not shown) was confirmed in the human $CD56^+$ NK cells derived from any of the mice. The expression of perforin was also confirmed, but was slightly lower as compared with the results of mature NK cells differentiated in humans in vivo (data not shown). As is evident from FIG. 7(b), the production of interferon gamma (IFNγ) was confirmed in the human NK cells derived from any of the mice by stimulation with PMA/ionomycin.

Example 9

(Generation of Human Peripheral Blood-Derived $hCD56^+$ NK Cell-Transplanted NOG-hIL-15 Tg Mouse)

Human peripheral blood-derived $CD56^+$ NK cells were transplanted to the 8 to 12 weeks old adult NOG-hIL-15 Tg mice. The mice were irradiated with 2.5 Gy X-ray. Within hours after the irradiation, 1 to $2 \times 10^6$ human peripheral blood-derived $hCD56^+$ NK cells were transplanted via the tail vein to generate human peripheral blood-derived $CD56^+$ NK cell-transplanted NOG-hIL-15 Tg mice (hereinafter, also referred to as "peripheral blood-transplanted hIL-15 mice"). Similarly, human peripheral blood-derived $hCD56^+$ NK cell-transplanted NOG-hIL-2 Tg mice (hereinafter, also referred to as "peripheral blood-transplanted hIL-2 mice") were generated. Human peripheral blood-derived $hCD56^+$ NK cell-transplanted NOG mice (hereinafter, also referred to as "peripheral blood-transplanted non-Tg mice") were generated and used as negative controls.

Example 10

(Study on Cells in Peripheral Blood of Peripheral Blood-Transplanted hIL-15 Mouse)

Blood was collected after a lapse of 3 weeks after the transplantation. Cells in the blood were stained with respective specific antibodies against an antigen mCD45, an antigen hCD3, an antigen hCD16, an antigen hCD45, and an antigen hCD56, followed by flow cytometry measurement to analyze the ratio of human leucocyte chimeras in the blood of each mouse. A fraction positive to the antigen hCD45 serving as a marker for human leucocytes (mCD45 serving as a marker for mouse leucocytes: negative fraction) was gated, and patterns for the antigen hCD56 serving as a marker for human NK cells and the antigen hCD3 serving as a marker for T cells were further developed. $hCD45^+CD56^+$ NK cells were gated, and patterns for the antigen hCD56 and the antigen hCD16 were further developed to analyze the proportion of $hCD56^+ hCD16^+$ NK cells. In order to confirm contamination by human T cells, the proportion of $hCD45^+ hCD3^+$ T cells was also confirmed. The results are shown in FIG. 8.

(Results)

In FIG. 8, "PBMC" denotes mononuclear cells in healthy human-derived human peripheral blood. "$CD56^+$ sorted (pre-transfer)" denotes $hCD56^+$ NK cells isolated from PBMC before transplantation. "After transfer (3w)" denotes the peripheral blood of the peripheral blood-transplanted hIL-15 mice after a lapse of 3 weeks after the transplantation. In the peripheral blood-transplanted hIL-15 mice after a lapse of 3 weeks after the transplantation, the $CD56^+ CD16^+$ NK cell fraction accounted for a large portion (99.7%) of the $hCD45^+$ human leucocytes. In "PBMC" and "$CD56^+$ sorted (pre-transfer)" as well, the mature NK cells in human peripheral blood accounted for 90% or more of the $hCD56^+ hCD16^+$ fraction in $hCD45^+$ human leucocytes. Therefore, it can be concluded that the transplanted $hCD56^+$ NK cells were engrafted and proliferated even after a lapse of 3 weeks after the transplantation while maintaining the property of being $hCD56^+ hCD16^+$ NK cells similar to those in the mononuclear cells of healthy human-derived human peripheral blood.

Example 11

Blood was collected over time after the transplantation, and the ratios of NK cells and T cells to mononuclear cells were measured. From the 3 types of peripheral blood-transplanted mice, peripheral blood was collected after a lapse of predetermined durations after the transplantation. Cells in the peripheral blood were stained with respective specific antibodies against an antigen hCD56 serving as a marker for NK cells, an antigen hCD45 serving as a marker for leucocytes, and an antigen hCD3 serving as a marker for T cells, followed by flow cytometry measurement to analyze the ratio of human leucocyte chimeras in the mouse blood. FIG. 9(a) shows the ratio (%) of the number of NK cells to mononuclear cells (MNC), and FIG. 9(b) shows the ratio (%) of the number of T cells to MNC. FIG. 9(c) shows the number of NK cells (/μL) in the blood of the peripheral blood-transplanted hIL-15 mice, and FIG. 9(d) shows the number of NK cells (/μL) in the blood of the peripheral blood-transplanted non-Tg mice.

(Results)

As is evident from FIG. 9(a), the NK cells accounted for approximately 30 to approximately 46% of mononuclear cells after a lapse of 2 weeks after the transplantation, approximately 10 to approximately 20% thereof after a lapse of 4 weeks, and approximately 8 to approximately 15% thereof after a lapse of 6 weeks, in the peripheral blood-transplanted hIL-15 mice. As is evident from FIG. 9(b), the NK cells remained at less than 10% after a lapse of 4 weeks after the transplantation when the largest increase was observed, in the peripheral blood-transplanted hIL-2 mice. The T cells were hardly detected in the peripheral blood-transplanted hIL-15 mice, whereas the T cells accounted for approximately 18 to approximately 23% after a lapse of 3 to 4 weeks after the transplantation in the peripheral blood-transplanted hIL-2 mice. In the peripheral blood-transplanted non-Tg mice, both the NK cells and the T cells were hardly detected. From these results, it was confirmed that, in the peripheral blood-transplanted hIL-2 mice, NK cells did not proliferate in the blood, while a very small number of T cells contaminating transplanted cells proliferated. Therefore, only the peripheral blood-transplanted hIL-15 mice were studied in subsequent experiments. In the human peripheral blood hIL-15 Tg mice, the number of human NK cells in the blood increased gradually and increased to 8000 cells/μL after a lapse of 4 to 5 weeks after the transplantation. Although the number of human NK cells then decreased gradually, approximately 40 cells/μL were confirmed even after a lapse of 24 weeks after the transplantation (see FIG. 9(c)). In the human peripheral blood non-Tg mice, the maximum value of approximately 40 cells/uL was confirmed after a lapse of 2 weeks after the transplantation, and proliferation thereof was hardly observed (see FIG. 9(d)).

Example 12

(Study on Change in Human Mature NK Cell Sub-Population)

Human NK cells are known to include a sub-population that occupies a hCD56$^+$ hCD16$^+$ fraction and is dedicated to cytotoxic ability, and a sub-population that occupies a hCD56$^+$ hCD16$^-$ fraction and is dedicated to the ability to produce cytokines. In order to confirm a fraction where human mature NK cells transplanted in the peripheral blood-transplanted hIL-15 mice would proliferate, time-dependent change in cell sub-population was analyzed. The results are shown in FIG. 10.

(Results)

As is evident from FIG. 10, the hCD56$^+$ hCD16$^+$ fraction maintained almost 90% or more from 1 week through 8 weeks after the transplantation. On the other hand, the hCD56$^+$ hCD16$^-$ fraction accounted for approximately 11% after a lapse of 1 week after the transplantation, but then decreased gradually. Thus, the sub-population dedicated to cytotoxic ability (hCD56$^+$hCD16$^+$ fraction) was confirmed to proliferate in the peripheral blood of the peripheral blood-transplanted hIL-15 mice.

Example 13

[Preparation of Frozen Peripheral Blood hIL-15 Mouse]

Human peripheral blood-derived hCD56$^+$ frozen NK cells were thawed and transplanted to the 8 to 12 weeks old adult NOG-hIL-15 Tg mice. The mice were irradiated with 2.5 Gy X-ray. After a lapse of 24 hours after the irradiation, 1 to 2×10$^6$ thawed human peripheral blood-derived CD56$^+$ NK cells were transplanted via the tail vein to generate human peripheral blood-derived CD56$^+$ frozen NK cell-transplanted NOG-hIL-15 Tg mice (hereinafter, also referred to as "frozen peripheral blood hIL-15 mice").

Example 14

(Study on Ability of Human Cells to Differentiate in Peripheral Blood of Frozen Peripheral Blood hIL-15 Mouse)

From the frozen peripheral blood hIL-15 mice, blood was collected over time after the transplantation. Cells in the blood were stained with each specific antibody, followed by flow cytometry measurement to analyze the ratio of human leucocyte chimeras in the mouse blood. A fraction positive to the antigen hCD45 serving as a marker for human leucocytes (mCD45 serving as a marker for mouse leucocytes: negative fraction) was gated, and patterns for the antigen hCD56 serving as a marker for human NK cells and the antigen hCD3 serving as a marker for T cells, and patterns for the antigen hCD56 and the antigen hCD16 were further developed to analyze the proportions of human CD56$^+$ NK cells and human CD56$^+$ CD16$^+$ NK cells. In order to confirm contamination by human T cells, the proportion of hCD45$^+$hCD3$^+$ T cells was also confirmed. The results are shown in FIGS. 11 and 12.

(Results 1)

As is evident from "Frozen PB-NK (Pre-transfer)" which denotes untransplanted frozen human CD56$^+$ NK cells in FIG. 11, mature NK cells in human peripheral blood after thawing accounted for 85.2% of the hCD16$^+$hCD56$^+$ fraction. The mature NK cells also accounted for 81.3% of the hCD16$^+$hCD56$^+$ fraction in the frozen peripheral blood hIL-15 mice at 4 weeks after the transplantation of the frozen human CD56$^+$ NK cells. Therefore, it was able to be confirmed that the transplanted thawed human NK cells were engrafted and proliferated even after a lapse of 4 weeks after the transplantation in the NOG-hIL-15 Tg mice, as in the fresh blood-derived human NK cell transplantation experiment.

(Results 2)

As is evident from FIG. 12, the sub-population that occupied the CD56$^+$ CD16$^+$ fraction proliferated selectively, increased rapidly from 1 week through 2 weeks after the transplantation, and decreased gradually at and after 3 weeks after the transplantation. On the other hand, the sub-population that occupied the CD56$^+$ CD16$^-$ fraction and was dedicated to the ability to produce cytokines hardly increased. Thus, it was confirmed that the CD56$^+$ CD16$^+$ NK cells dedicated to cytotoxic ability remarkably proliferated in the CD56$^+$ frozen NK cell-transplanted NOG-hIL-15 Tg mice.

Example 15

(Study on Human Cells in Each Tissue of Peripheral Blood-Transplanted hIL-15 Mouse)

The peripheral blood-transplanted hIL-15 mice were euthanized by the collection of whole blood under anesthesia after a lapse of 6 weeks after the transplantation. Then, bone marrow, the spleen, the liver, and the lung were harvested therefrom, followed by cell preparation. The cells were stained with each specific antibody, followed by flow cytometry measurement to analyze humanized cells in each mouse tissue. The results are shown in FIG. 13.

(Results)

As is evident from FIG. 13, the localization of human CD56$^+$ CD16$^+$ NK cells was confirmed in all of the spleen (SPL), the peripheral blood (PB), the liver (Liver), and the lung (Lung) of the peripheral blood-transplanted hIL-15 mice, but was not confirmed in the bone marrow (BM). This result was consistent with the results indicating that mature NK cells in human tissues are localized mainly in blood, the spleen, lymph node, tonsil, the liver, the lung, etc. whereas the mature NK cells are hardly present in bone marrow. However, this result was inconsistent with the results indicating the localization of human NK cells in bone marrow was confirmed in the stem cell-transplanted hIL-15 mice and the stem cell-transplanted hIL-2 mice. It was also confirmed that hNKp46, a NK cell marker, known as a member of the natural cytotoxicity receptor (NCR) family which induces the cytotoxic activity of NK cells was strongly expressed.

Example 16

(Expression Analysis of Cell Surface Molecule Specific for Human NK Cells)

The peripheral blood-transplanted hIL-15 mice were analyzed for whether or not the human NK cells isolated from the spleen after a lapse of 8 weeks after the transplantation would express the same specific cell surface molecules as those in mature NK cells in human tissues. The cells were stained with respective specific antibodies against antigens hNKG2A, hNKG2C, hNKG2D, hCD94, hNKp30, hNKp46, hNKp44, hNKp80, hCD57, hCD158a/h (killer immunoglobulin-like receptor: KIR), hCD158b (KIR), hCD158d (KIR), hCD158e (KIR), and hCD158f (KIR) known as cell surface molecules specific for mature NK cells in human tissues, followed by flow cytometry measurement to analyze the expression of the human NK cell-specific cell surface molecules. The results of the mice are shown in FIG. 14. A pattern stained with Isotype Ab is also shown as a negative control for each cell surface molecule.

(Results)

As is evident from FIG. 14, the expression of the antigens hNKG2A, hNKG2C, hNKG2D, hCD94, hNKp30, hNKp46, hNKp44, hNKp80, hCD57, hCD158a/h (killer immunoglobulin-like receptor: KIR), hCD158b (KIR), hCD158d (KIR), hCD158e (KIR), and hCD158f (KIR) known as cell surface molecules specific for mature NK cells in human tissues was confirmed. It was also confirmed that the human NK cells that proliferated in the peripheral blood-transplanted hIL-15 mice had almost the same surface molecule expression patterns of NK cells as in results of mature NK cells differentiated in humans in vivo (data not shown).

Example 17

(Verification of Ability of Human Peripheral Blood-Derived NK Cells to Secrete Cytotoxic Granule)

Whether or not the human NK cells isolated from the spleen of the peripheral blood-transplanted hIL-15 mice would have the ability to secrete cytotoxic granules and the ability to produce cytokines, as in mature NK cells differentiated in humans in vivo, was verified. The spleen was harvested from the peripheral blood-transplanted hIL-15 mice after a lapse of 8 weeks after the transplantation, followed by cell preparation. Human CD56$^+$ NK cells were isolated, cultured for 20 hours in the presence of Brefeldin A and in the presence of human IL-2 or IL-15 as a cytokine, and then intracellularly stained with fluorescently labeled antibodies FITC-anti-hgranzyme A antibody and FITC-anti-perforin antibody (manufactured by BioLegend, Inc.), followed by flow cytometry measurement. The results are shown in FIG. 15(a). Also, the isolated human CD56$^+$ NK cells were cultured in the presence of PMA/ionomycin and then intracellularly stained with a fluorescently labeled antibody PE-anti-hIFNg antibody (manufactured by BioLegend, Inc.), followed by flow cytometry measurement. The results are shown in FIG. 15(b).

(Results)

As is evident from FIG. 15(a), the expression of cytotoxic granules (granzyme A) comparable to results of mature NK cells differentiated in humans in vivo (data not shown) was also confirmed in the human CD56$^+$ NK cells derived from the NOG-hIL-15 Tg mice. However, perforin was hardly detectable even by stimulation with various cytokines. As is evident from FIG. 15(b), the production of interferon gamma (IFNγ) was confirmed by stimulation with PMA/ionomycin. This result indicated that the human NK cells that proliferated in the hIL-15 mice retained responsiveness to stimulatory factors (ability to produce cytokines).

(In Vitro Experiment on Suppression of Tumor Growth)

Whether the human NK cells isolated from the peripheral blood-transplanted hIL-15 mice would exhibit cytotoxic ability against target cells, was verified. The spleen was harvested from the peripheral blood-transplanted hIL-15 mice after a lapse of 8 weeks after the human NK cell transplantation, followed by cell preparation. hCD56$^+$ cells were isolated, cultured for 2 days in the presence of each cytokine (human IL-2, human IL-15, or a mixed composition of human IL-2 and human IL-15), and then cocultured for 4 hours with target tumor cells (highly human NK-sensitive tumor cell line K562), followed by the measurement of cytotoxic activity (cytotoxicity (%)) using the culture supernatant. The measurement method involved using the obtained culture supernatant and CytoTox 96 Non-radioactive Cytotoxicity Assay (manufactured by Promega Corp.) and conducting evaluation based on the degree of coloration attributed to the coupled enzyme reaction of a dead cell-derived cytoplasmic enzyme LDH released into the culture supernatant with the reaction substrate. The results are shown in FIG. 16.

(Results)

As is evident from FIG. 16, the human NK cells differentiated in the NOG-hIL-15 Tg mice exhibited the strongest cytotoxic activity when cultured in the presence of hIL-15. From this result, it was confirmed that human NK cells differentiated in the peripheral blood-transplanted hIL-15 mice can suppress the growth of human tumor in vitro, as in mature NK cells differentiated in humans in vivo.

(In Vivo Experiment on Suppression of Tumor Growth)

Whether the cytotoxic activity of the peripheral blood-transplanted hIL-15 mice against human tumor could be observed, was studied. The adult NOG-hIL-15 Tg mice were irradiated with 2.5 Gy X-ray for myelosuppression. Within 1 day after the irradiation, 2×10$^6$ human peripheral blood mononuclear cell (PBMC)-derived NK cells were iv transplanted to the mice to generate (hu-PB-NK hIL-15 Tg. NK cell-untransplanted (hIL-15-Tg) mice were used as negative controls. After a lapse of 4 weeks after the human PBMC-derived NK cell transplantation, 2.5×10$^5$ cells of a NK-sensitive human tumor cell line K562 were subcutaneously transplanted to the mice. The tumor size was measured over time. The results are shown in FIG. 17.

(Results)

As is evident from FIG. 17, the tumor size in the human NK cell-transplanted mice was on the order of 500 to 950 mm$^3$ at 21 days after the subcutaneous transplantation, whereas the tumor size in the NK cell-untransplanted (hIL-15-Tg) mice was on the order of 495 to 1730 mm$^3$. Thus, the tumor size in the human NK cell-transplanted mice was approximately ⅔ of the tumor size in the NK cell-untransplanted (hIL-15-Tg) mice. A tumor suppressive effect was confirmed in the human NK cell-transplanted group (d7-21; p<0.05). From these results, the peripheral blood-transplanted hIL-15 mice were confirmed to suppress the growth of human tumor in vivo.

INDUSTRIAL APPLICABILITY

The mouse of the present invention is very useful in the medical field as a humanized immunodeficient mouse that enables the functions of human NK cells to be studied for a long period after transplantation of human peripheral blood-derived human NK cells.

The invention claimed is:

1. An immunodeficient mouse whose genome comprises the nucleotide sequence of SEQ ID NO: 1,
   wherein the immunodeficient mouse is capable of secreting human IL-15, and comprises a human natural killer (NK) cell that expresses human CD56 and human CD16, wherein the NK cell is in the spleen, liver, and/or lung of the mouse but not in the bone marrow of the mouse.

2. The immunodeficient mouse according to claim 1, wherein the human NK cell expressing human CD56 and human CD16 also expresses hNKG2A, hNKG2C, hNKG2D, hCD94, hNKp30, hNKp46, hNKp44, hNKp80, hCD57, hCD158a/h, hCD158b, hCD158d, hCD158e, and/or hCD158f.

3. The immunodeficient mouse according to claim 2,
   wherein the immunodeficient mouse is transplanted with a human peripheral blood-derived human NK cell expressing human CD56 and human CD16,
   wherein the human NK cell expressing human CD56 and human CD16 is engrafted and proliferated in the immunodeficient mouse, and the NK cell can be isolated from the mouse,
   and wherein the isolated NK cell is capable of suppressing growth of human tumor in vitro in the presence of a human IL-15.

4. The immunodeficient mouse according to claim 1, wherein the immunodeficient mouse is transplanted with a human peripheral blood-derived human NK cell expressing human CD56 and human CD16,
   wherein the human NK cell expressing human CD56 and human CD16 is engrafted and proliferated in the immunodeficient mouse, and the NK cell can be isolated from the mouse,
   and wherein the isolated NK cell is capable of suppressing growth of human tumor in vitro in the presence of a human IL-15.

5. The immunodeficient mouse according to claim 1, wherein the immunodeficient mouse is capable of suppressing growth of a human tumor in vivo after the immunodeficient mouse is transplanted with the human tumor.

6. A method for generating the mouse of claim 1, comprising the following steps (1) to (5) sequentially:
   (1) introducing a DNA comprising a nucleotide sequence represented by SEQ ID NO: 1 to a vector comprising a region necessary for inserting a DNA consisting of the nucleotide sequence represented by SEQ ID NO: 1 to a mouse genomic DNA, thereby generating a vector for DNA preparation for injection into a mouse fertilized egg having the DNA comprising the nucleotide sequence represented by SEQ ID NO: 1;
   (1-1) optionally preparing a DNA fragment for injection into fertilized eggs wherein the DNA fragment comprises the DNA consisting of the nucleotide sequence represented by SEQ ID NO: 1, and a region necessary for insertion of the DNA comprising the nucleotide sequence represented by SEQ ID NO: 1 to mouse genomic DNA;
   (2) injecting the vector generated in the step (1) and/or the vector fragment prepared in the step (1-1) into a fertilized egg of an interleukin 2 receptor γ chain gene (IL-2Rγ)-knockout mouse, thereby generating an injected-fertilized egg;
   (3) culturing the injected-fertilized egg generated in the step (2), thereby generating a newborn mouse;
   (4) determining whether or not the DNA comprising the nucleotide sequence represented by SEQ ID NO: 1 is inserted in genomic DNA of a NOD-IL-2rγ$^{null}$ mouse among the mouse generated in the step (3);
   (5) determining whether or not the mouse determined in the step (4) that the DNA comprising the nucleotide sequence represented by SEQ ID NO: 1 is inserted in genomic DNA of the NOD-IL-2rγ$^{null}$ mouse secretes hIL-15, thereby selecting a hIL-15-secreting mouse as a NOD-IL-2rγ$^{null}$-hIL-15 Tg mouse.

* * * * *

SEQUENCE LISTING

<160> NUMBER OF SEQ ID NOS: 8

<210> SEQ ID NO 1
<211> LENGTH: 440
<212> TYPE: DNA
<213> ORGANISM: Artificial
<220> FEATURE:
<223> OTHER INFORMATION: hIL-2SPcDNA-hIL-15cDNA
<220> FEATURE:
<221> NAME/KEY: misc_feature
<223> OTHER INFORMATION: Inventor: ITO, Mamoru; KATANO, Ikumi

<400> SEQUENCE: 1

| | | | | | | |
|---|---|---|---|---|---|---|
| tcacagtaac | ctcaactcct | gccacaatgt | acaggatgca | actcctgtct | tgcattgcac | 60 |
| taagtcttgc | acttgtcaca | aacagtgcaa | ctagtaactg | ggtgaatgta | ataagtgatt | 120 |
| tgaaaaaaat | tgaagatctt | attcaatcta | tgcatattga | tgctacttta | tatacggaaa | 180 |
| gtgatgttca | ccccagttgc | aaagtaacag | caatgaagtg | ctttctcttg | gagttacaag | 240 |
| ttatttcact | tgagtccgga | gatgcaagta | ttcatgatac | agtagaaaat | ctgatcatcc | 300 |
| tagcaaacaa | cagtttgtct | tctaatggga | atgtaacaga | atctggatgc | aaagaatgtg | 360 |
| aggaactgga | ggaaaaaaat | attaaagaat | ttttgcagag | ttttgtacat | attgtccaaa | 420 |
| tgttcatcaa | cacttcttga | | | | | 440 |

<210> SEQ ID NO 2
<211> LENGTH: 35
<212> TYPE: DNA
<213> ORGANISM: Artificial
<220> FEATURE:
<223> OTHER INFORMATION: primer

<400> SEQUENCE: 2
atagcggccg ctcacagtaa cctcaactcc tgcaa    35

<210> SEQ ID NO 3
<211> LENGTH: 30
<212> TYPE: DNA
<213> ORGANISM: Artificial
<220> FEATURE:
<223> OTHER INFORMATION: primer

<400> SEQUENCE: 3
atcactagtt gcactgtttg tgacaagtgc    30

<210> SEQ ID NO 4
<211> LENGTH: 31
<212> TYPE: DNA
<213> ORGANISM: Artificial
<220> FEATURE:
<223> OTHER INFORMATION: primer

<400> SEQUENCE: 4
gggactagta actgggtgaa tgtaataagt g    31

<210> SEQ ID NO 5
<211> LENGTH: 49
<212> TYPE: DNA
<213> ORGANISM: Artificial
<220> FEATURE:
<223> OTHER INFORMATION: primer

<400> SEQUENCE: 5
caactagttc acttgtcacg tcgtccttgt agtcagaagt gttgatgaa    49

<210> SEQ ID NO 6
<211> LENGTH: 1840
<212> TYPE: DNA
<213> ORGANISM: Artificial
<220> FEATURE:
<223> OTHER INFORMATION: DNA fragment

<400> SEQUENCE: 6

| | | | | | |
|---|---|---|---|---|---|
| ccagctggcg | aaaggggat | gtgctgcaag | gcgattaagt | tgggtaacgc | cagggttttc | 60 |
| ccagtcacga | cgttgtaaaa | cgacggccag | tgaattcgag | cttgcatgcc | tgcaggtcgt | 120 |
| tacataactt | acggtaaatg | gcccgcctgg | ctgaccgccc | aacgaccccc | gcccattgac | 180 |
| gtcaataatg | acgtatgttc | ccatagtaac | gccaataggg | actttccatt | gacgtcaatg | 240 |
| ggtggagtat | ttacggtaaa | ctgcccactt | ggcagtacat | caagtgtatc | atatgccaag | 300 |
| tacgccccct | attgacgtca | atgacggtaa | atggcccgcc | tggcattatg | cccagtacat | 360 |
| gaccttatgg | gactttccta | cttggcagta | catctacgta | ttagtcatcg | ctattaccat | 420 |
| ggtgatgcgg | ttttggcagt | acatcaatgg | gcgtggatag | cggtttgact | cacggggatt | 480 |
| tccaagtctc | cacccccattg | acgtcaatgg | gagtttgttt | tggcaccaaa | atcaacggga | 540 |
| ctttccaaaa | tgtcgtaaca | actccgcccc | attgacgcaa | atgggcggta | ggcgtgtacg | 600 |
| gtgggaggtc | tatataagca | gagctcgttt | agtgaaccgt | cagatcgcct | ggagacgcca | 660 |
| tccacgctgt | tttgacctcc | atagaagaca | ccggaccga | tccagcctcc | ggactctaga | 720 |
| ggatccggta | ctcgaggaac | tgaaaaacca | gaaagttaac | tggtaagttt | agtcttttg | 780 |
| tcttttattt | caggtcccgg | atccggtggt | ggtgcaaatc | aaagaactgc | tcctcagtgg | 840 |
| atgttgcctt | tacttctagg | cctgtacgga | agtgttactt | ctgctctaaa | agctgcggaa | 900 |
| ttgtacccgc | ggccgctcac | agtaacctca | actcctgcca | caatgtacag | gatgcaactc | 960 |
| ctgtcttgca | ttgcactaag | tcttgcactt | gtcacaaaca | gtgcaactag | taactgggtg | 1020 |
| aatgtaataa | gtgatttgaa | aaaaattgaa | gatcttattc | aatctatgca | tattgatgct | 1080 |
| actttatata | cggaaagtga | tgttcacccc | agttgcaaag | taacagcaat | gaagtgcttt | 1140 |
| ctcttggagt | tacaagttat | ttcacttgag | tccggagatg | caagtattca | tgatacagta | 1200 |
| gaaaatctga | tcatcctagc | aaacaacagt | ttgtcttcta | atgggaatgt | aacagaatct | 1260 |
| ggatgcaaag | aatgtgagga | actggaggaa | aaaatatta | aagaatttt | gcagagtttt | 1320 |
| gtacatattg | tccaaatgtt | catcaacact | tctgactaca | aggacgacga | tgacaagtga | 1380 |
| actagttgat | aagccgaatt | ctgcagatat | ccatcacact | ggcggccgcg | ggatccaga | 1440 |
| catgataaga | tacattgatg | agtttggaca | aaccacaact | agaatgcagt | gaaaaaaatg | 1500 |
| ctttatttgt | gaaatttgtg | atgctattgc | tttatttgta | accattataa | gctgcaataa | 1560 |
| acaagttaac | aacaacaatt | gcattcattt | tatgtttcag | gttcagggg | aggtgtggga | 1620 |
| ggttttttcg | gatcctctag | agtcgacctg | caggcatgca | agcttggcgt | aatcatggtc | 1680 |
| atagctgttt | cctgtgtgaa | attgttatcc | gctcacaatt | ccacacaaca | tacgagccgg | 1740 |
| aagcataaag | tgtaaagcct | ggggtgccta | atgagtgagc | taactcacat | taattgcgtt | 1800 |
| gcgctcactg | cccgctttcc | agtcgggaaa | cctgtcgtgc | | | 1840 |

<210> SEQ ID NO 7
<211> LENGTH: 35
<212> TYPE: DNA
<213> ORGANISM: Artificial
<220> FEATURE:
<223> OTHER INFORMATION: primer

```
<400> SEQUENCE: 7
atagcggccg ctcacagtaa cctcaactcc tgcca                          35

<210> SEQ ID NO 8
<211> LENGTH: 39
<212> TYPE: DNA
<213> ORGANISM: Artificial
<220> FEATURE:
<223> OTHER INFORMATION: primer

<400> SEQUENCE: 8
caactagttc acttgtcatc gtcgtccttg tagtcagaa                      39
```